(12) United States Patent
Hunig

(10) Patent No.: US 8,389,016 B2
(45) Date of Patent: Mar. 5, 2013

(54) USE OF A CD28 BINDING SUBSTANCE FOR MAKING A PHARMACEUTICAL COMPOSITION

(75) Inventor: Thomas Hunig, Wurzberg (DE)

(73) Assignee: Theramab LLC, Moscow (RU)

( * ) Notice: Subject to any disclaimer, the term of this patent is extended or adjusted under 35 U.S.C. 154(b) by 176 days.

(21) Appl. No.: 12/251,039

(22) Filed: Oct. 14, 2008

(65) Prior Publication Data

US 2009/0246204 A1    Oct. 1, 2009

Related U.S. Application Data

(63) Continuation of application No. 11/585,484, filed on Oct. 24, 2006, now abandoned, which is a continuation of application No. 10/389,679, filed on Mar. 13, 2003, now abandoned.

(30) Foreign Application Priority Data

Mar. 13, 2002   (DE) .................................. 102 12 108

(51) Int. Cl.
*A61K 35/14* (2006.01)
(52) U.S. Cl. ...................................................... 424/529
(58) Field of Classification Search .................. None
See application file for complete search history.

(56) References Cited

U.S. PATENT DOCUMENTS 6,987,171 B1     1/2006   Hunig ...................... 530/388.75
2003/0166860 A1  9/2003   Hunig et al. .................. 530/350

FOREIGN PATENT DOCUMENTS

WO     WO 98/54225    12/1998

OTHER PUBLICATIONS

Blazar et al., J. Immunol., 1996, 157:3250-3259.
Nature, 2006, vol. 440, pp. 388-389.
Nature, 2006, vol. 440, pp. 855-856.
Mehrishi, Jitendra et al., "Some aspects of the recombinantly expressed humanised superagonist anti-CD28 mAb, TGN1412 trial catastrophe lessons to safeguard mAbs and vaccine trials," Vaccine, 2007, 25:3517-3523.

*Primary Examiner* — Ilia Ouspenski
(74) *Attorney, Agent, or Firm* — Keum J. Park, Esq.; Mayer & Williams PC

(57) ABSTRACT

The invention relates to the use of a CD28-specific superagonistic monoclonal antibody (mAb) or of a mimicry compound hereto for making a pharmaceutical composition for the induction and/or multiplication of regulatory T cells.

2 Claims, 24 Drawing Sheets

Figure 1A:
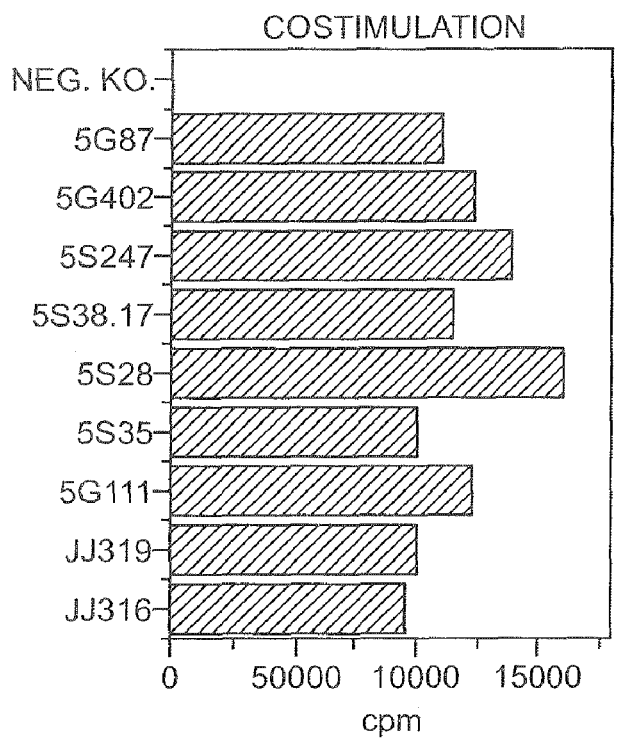

 = MOUSE
 = RAT
JJ316　　JJ319
m/r CD28
1-37
  
r/m CD28
1-37
  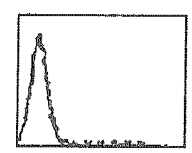
m/r CD28
1-37
  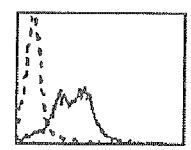
m CD28
A64V, E65G
  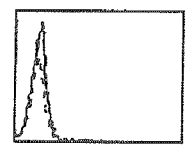
m CD28
S62P,
A64V, E65G
  
FIG. 3

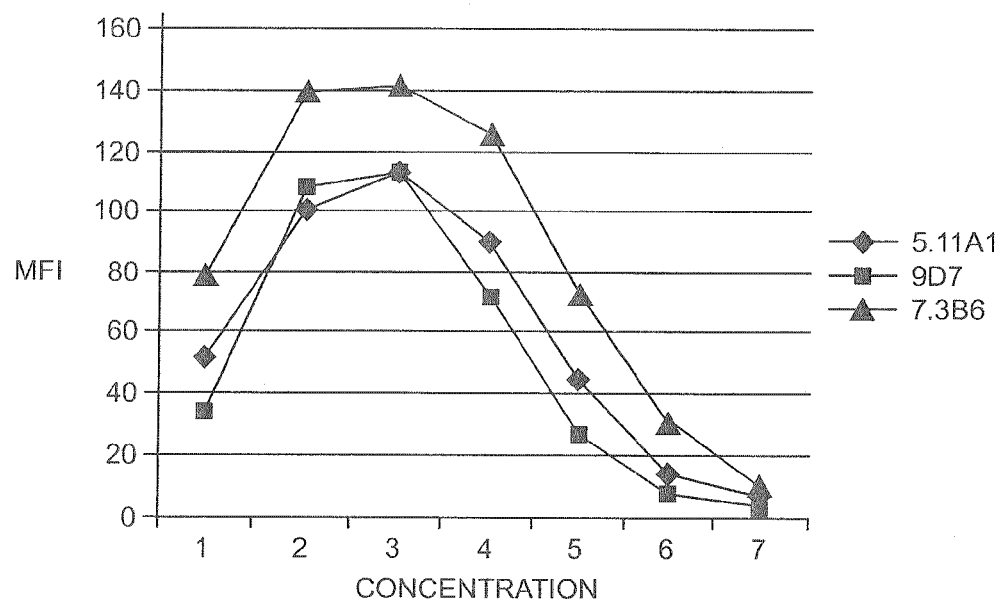
FIG. 4a
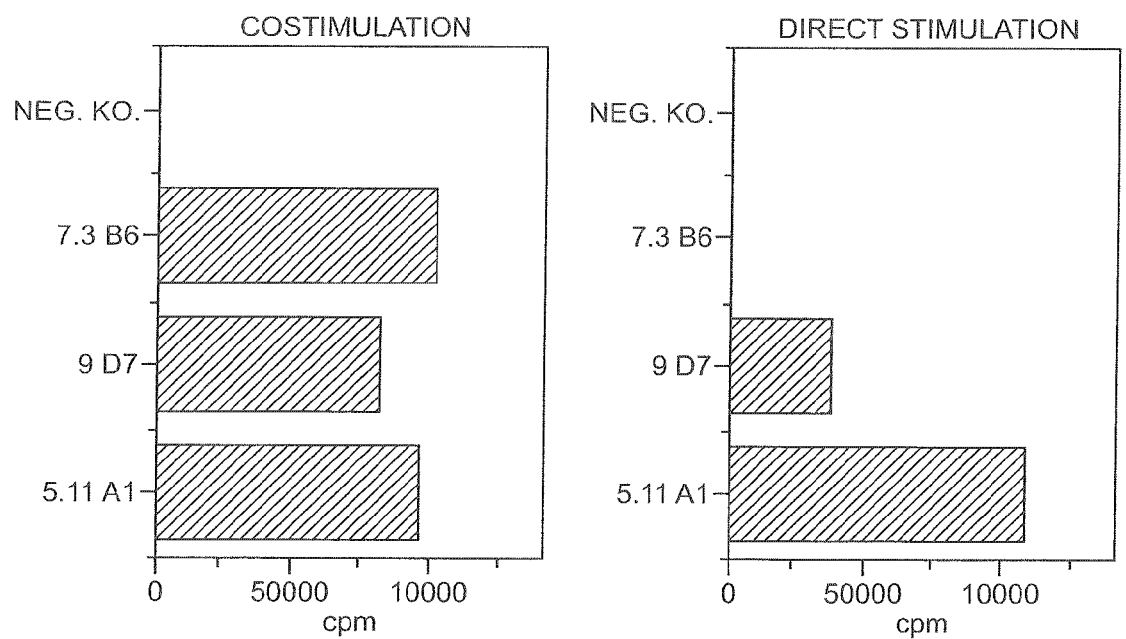
FIG. 4b
FIG. 4c

```
  1                                                           50
GATATCCAGA  CGACACAGAC  TACATCCTCC  CTGTCTGCCT  CTCTGGGAGA
 51                                                          100
CAGAGTCACC  ATCAGTTGCA  GGGCAGGTCA  GGACATTAGT  AATTATTTAA
101                                                          150
ACTGGTATCA  GCAGAAACCA  GATGGAACTG  TTAAGCTCCT  GATCTACTAC
151                                                          200
ACATCAAGAT  TACACTCAGG  AGTCCCATCA  AGGTTCAGTG  GCAGTGGGTC
201                                                          250
TGGAACAGAT  TATTCTCTCA  CCATTAGCAA  CCTGGAGCAA  GAAGATATTG
251                                                          300
CCACTTACTT  TTGCCAACAG  GGTCATACGC  TTCCGTGGAC  GTTCGGTGGA
301                   321
GGCACCAAGC  TGGAAATCAA  A
```

FIG. 8a

```
  1                                                           50
DIQTTQTTSS  LSASLGDRVT  ISCRAGQDIS  NYLNWYQQKP  DGTVKLLIYY
 51                                                          100
TSRLHSGVPS  RFSGSGSGTD  YSLTISNLEQ  EDIATYFCQQ  GHTLPWTFGG
101    107
GTKLEIK
```

FIG. 8b

```
  1                                                           50
DVQLQESGPG  LVKPSQSLSL  TCTVTGYSIT  SDYAWNWIRQ  FPGNKLEWMG
 51                                                          100
YIRYSGSTSY  NPSLKSRISI  TRDTSKNQFF  LQLNSVTTED  TATYYCARDW
101                   121
PRPSYWYFDV  WGAGTTVTVS  S
```

FIG. 8d

```
  1                                                                50
  GATGTGCAGC TTCAGGAGTC GGGACCTGGC CTGGTGAAAC CTTCTCAGTC
 51                                                               100
  TCTGTCCCTC ACCTGCACTG TCACTGGCTA CTCAATCACC AGTGATTATG
101                                                               150
  CCTGGAACTG GATCCGGCAG TTTCCAGGAA ACAAACTGGA GTGGATGGGC
151                                                               200
  TACATAAGAT ACAGTGGTAG TACTAGCTAC AATCCATCTC TCAAAAGTCG
201                                                               250
  AATCTCTATC ACTCGAGACA CATCCAAGAA CCAGTTCTTC CTGCAGTTGA
251                                                               300
  ATTCTGTGAC TACTGAGGAC ACAGCCACAT ATTACTGTGC AAGAGATTGG
301                                                               350
  CCGCGACCGA GCTACTGGTA CTTCGATGTC TGGGGCGCAG GGACCACGGT
351        363
  CACCGTCTCC TCA
```

FIG. 8c

```
  1                                                                50
  CAGGTCCAAC TGCAGCAGTC CGGACCTGAG CTGGTGAAGC CGGGGACTTC
 51                                                               100
  AGTGAGGATT TCCTGCGAGG CTTCTGGCTA CACCTTCACA AGCTACTATA
101                                                               150
  TACACTGGGT GAAACAGAGG CCTGGACAGG GACTTGAGTG GATTGGATGT
151                                                               200
  ATTTATCCTG GAAATGTCAA TACTAACTAT AATGAGAAGT TCAAGGACAA
201                                                               250
  GGCCACACTG ATTGTAGACA CATCCTCCAA CACTGCCTAC ATGCAGCTCA
251                                                               300
  GCAGAATGAC CTCTGAGGAC TCTGCGGTCT ATTTCTGTAC AAGATCACAC
301                                                               350
  TACGGCCTCG ACTGGAACTT CGATGTCTGG GGCGCAGGGA CCACGGTCAC
351       360
  CGTCTCCTCA
```

FIG. 8e

```
  1                                                            50
  QVQLQQSGPE LVKPGTSVRI SCEASGYTFT SYYIHWVKQR PGQGLEWICC
 51                                                           100
  IYPGNVNTNY NEKFKDKATL IVDTSSNTAY MQLSRMTSED SAVYFCTRSH
101        120
  YGLDWNFDVW GAGTTVTVSS
```

FIG. 8f

```
  1                                                            50
  GACATCCAGA TGAACCAGTC TCCATCCAGT CTGTCTGCAT CCCTTGGAGA
 51                                                           100
  CACAATTACC ATCACTTGCC ATGCCAGTCA AACATTTAT GTTTGGTTAA
101                                                           150
  ACTGGTACCA GCAGAAACCA GGAAATATTC CTAAACTCTT GATCTATAAG
151                                                           200
  GCTTCCAACC TGCACACAGG CGTCCCATCA AGGTTTAGTG GCAGTGGATC
201                                                           250
  TGGAACAGGC TTCACATTAA CCATCAGCAG CCTGCAGCCT GAAGACATTG
251                                                           300
  CCACTTACTA CTGTCAACAG GGTCAAACTT ATCCGTACAC GTTCGGAGGG
301        321
  GGGACCAAGC TGGAAATAAA A
```

FIG. 8g

```
  1                                                            50
  DIQMNQSPSS LSASLGDTIT ITCHASQNIY VWLNWYQQKP GNIPKLLIYK
 51                                                           100
  ASNLHTGVPS RFSGSGSGTG FTLTISSLQP EDIATYYCQQ GQTYPYTFGG
101    107
  GTKLEIK
```

FIG. 8h

```
1                                                                15
  D   I   Q   M   T   Q   S   P   S   A   L   S   A   S   V
Asp Ile Gln Met Thr Gln Ser Pro Ser Ser Leu Ser Ala Ser Val 16                                                               30
  G   D   R   V   T   I   T   C   H   A   S   Q   N   I   Y
Gly Asp Arg Val Thr Ile Thr Cys His Ala Ser Gln Asn Ile Tyr 31                                                               45
  V   W   L   N   W   Y   Q   Q   K   P   G   K   A   P   K
Val Trp Leu Asn Trp Tyr Gln Gln Lys Pro Gly Lys Ala Pro Lys 46                                                               60
  L   L   I   Y   K   A   S   N   L   H   T   G   V   P   S
Leu Leu Ile Tyr Lys Ala Ser Asn Leu His Thr Gly Val Pro Ser 61                                                               75
  R   F   S   G   S   G   S   G   T   D   F   T   L   T   I
Arg Phe Ser Gly Ser Gly Ser Gly Thr Asp Phe Thr Leu Thr Ile 76                                                               90
  S   S   L   Q   P   E   D   F   A   T   Y   Y   C   Q   Q
Ser Ser Leu Gln Pro Glu Asp Phe Ala Thr Tyr Tyr Cys Gln Gln 91                                                              105
  G   Q   T   Y   P   Y   T   F   G   G   G   T   K   V   E
Gly Gln Thr Tyr Pro Tyr Thr Phe Gly Gly Gly Thr Lys Val Glu 106 107
  I   K
Ile Lys
```

FIG. 8i

```
  1                                                                    15
  Q   V   Q   L   V   Q   S   G   A   E   V   K   K   P   G
 Gln Val Gln Leu Val Gln Ser Gly Ala Glu Val Lys Lys Pro Gly 16                                                                    30
  A   S   V   K   V   S   C   K   A   S   G   Y   T   F   T
 Ala Ser Val Lys Val Ser Cys Lys Ala Ser Gly Tyr Thr Phe Thr 31                                                                    45
  S   Y   Y   I   H   W   V   R   Q   A   P   G   Q   G   L
 Ser Tyr Tyr Ila His Trp Val Arg Gln Ala Pro Gly Gln Gly Leu 46                                                                    60
  E   W   I   G   C   I   W   P   G   N   V   N   T   N   Y
 Glu Trp Ile Gly Cys Ile Tyr Pro Gly Asn Val Asn Thr Asn Tyr 61                                                                    75
  N   E   K   F   K   D   R   A   T   L   T   V   D   T   S
 Asn Glu Lys Phe Lys Asp Arg Ala Thr Leu Thr Val Asp Thr Ser 76                                                                    90
  I   S   T   A   Y   M   E   L   S   R   L   R   S   D   D
 Ile Ser Thr Ala Tyr Met Glue Leu Ser Arg Leu Arg Ser Asp Asp 91                                                                   105
  T   A   V   Y   F   C   T   R   S   H   Y   G   L   D   W
 Thr Ala Val Tyr Phe Cys Thr Arg Ser His Tyr Gly Leu Asp Trp 105                                                                  120
  N   F   D   V   W   G   Q   G   T   T   V   T   V   S   S
 Asn Phe Asp Val Trp Gly Gln Gly Thr Thr Val Thr Val Ser Ser
```

FIG. 8j

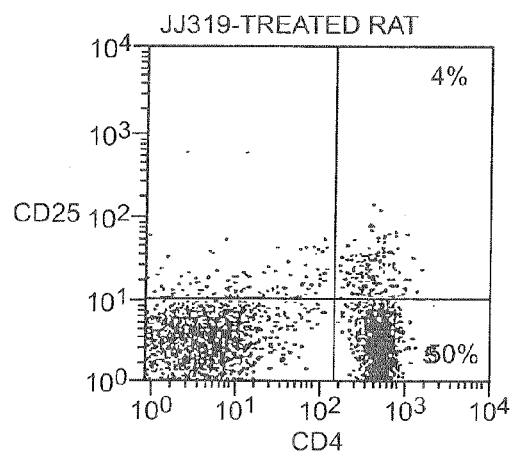
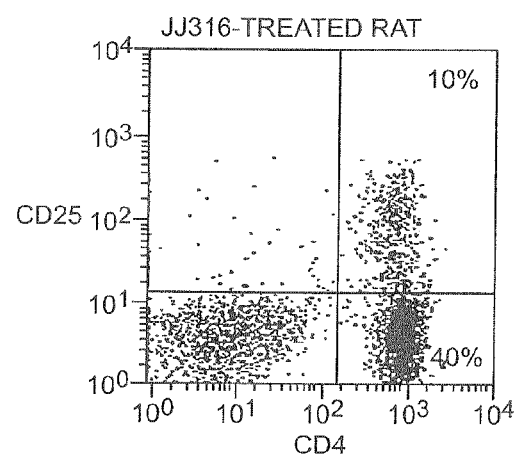
FIG. 9a    FIG. 9b
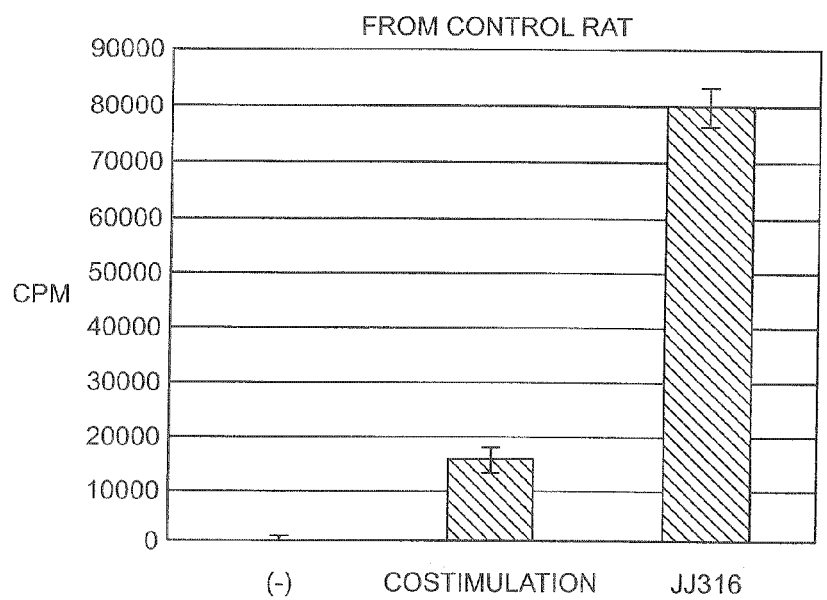
FIG. 11a

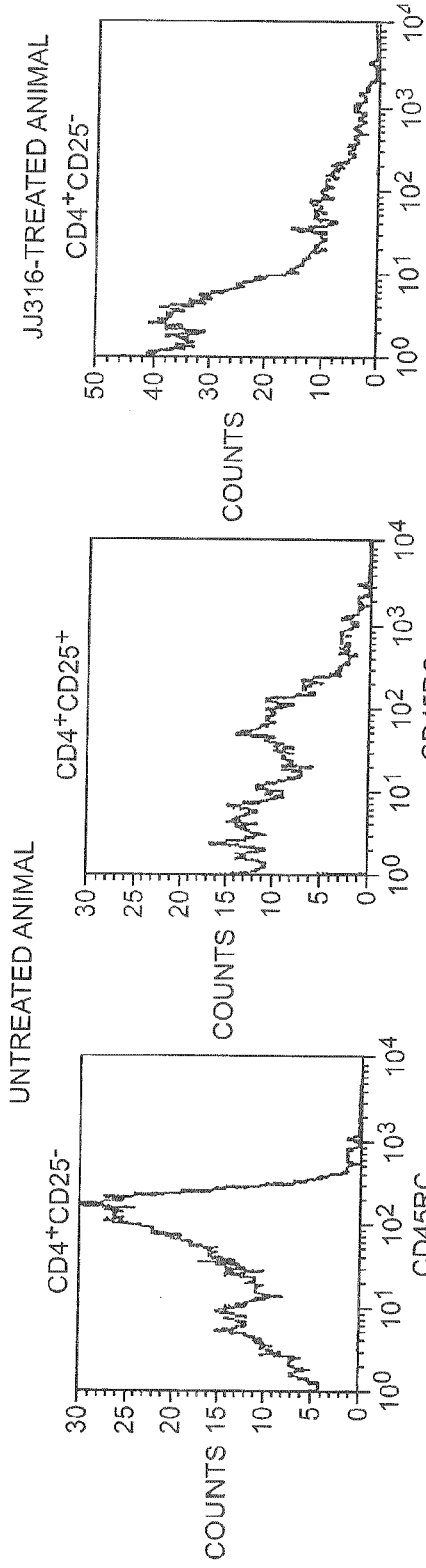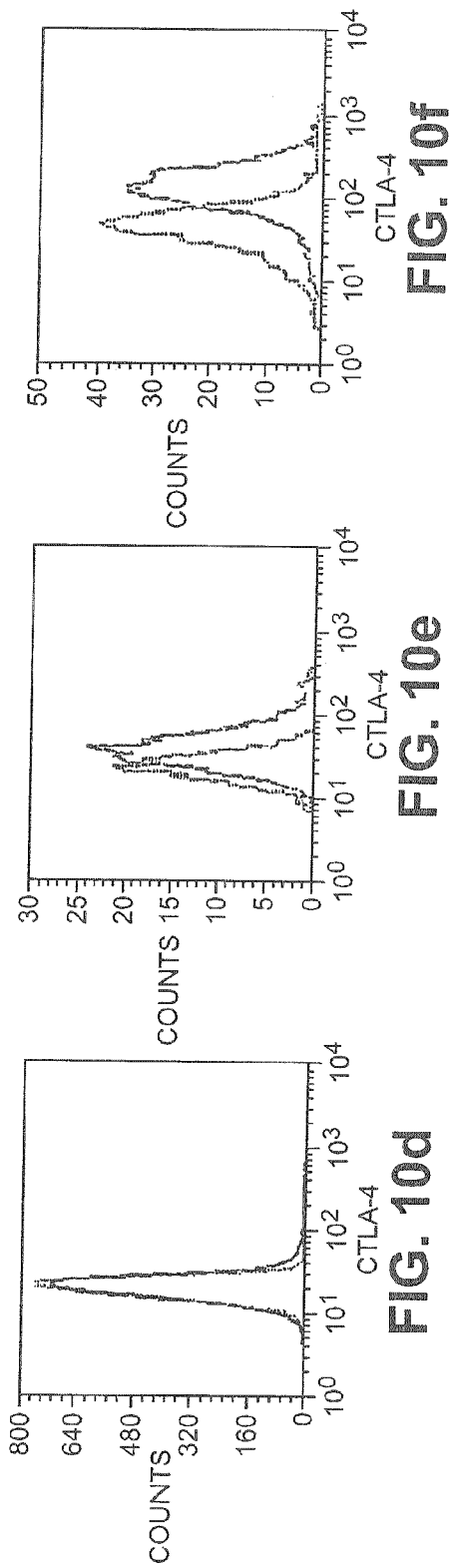

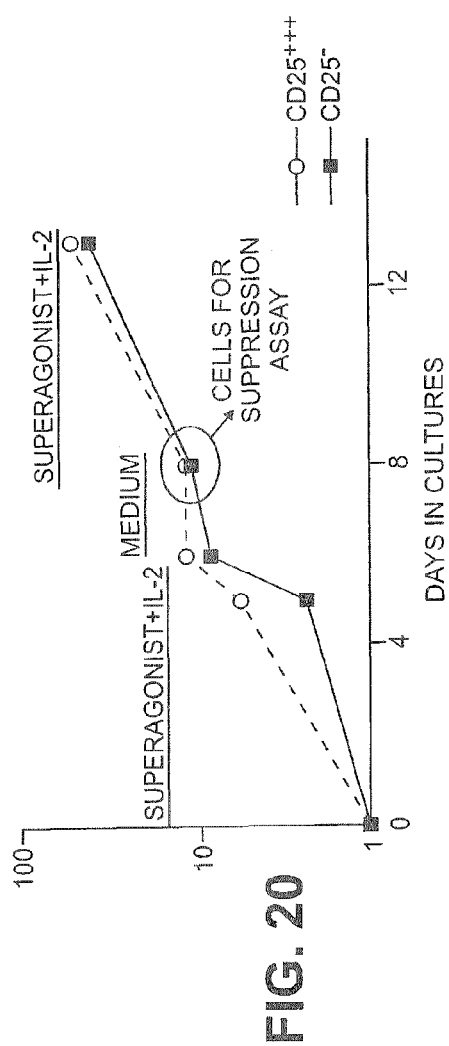
FIG. 20
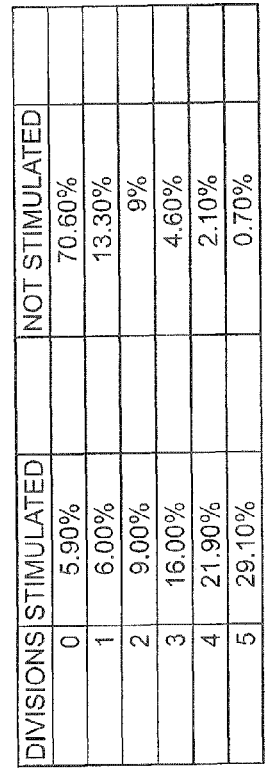
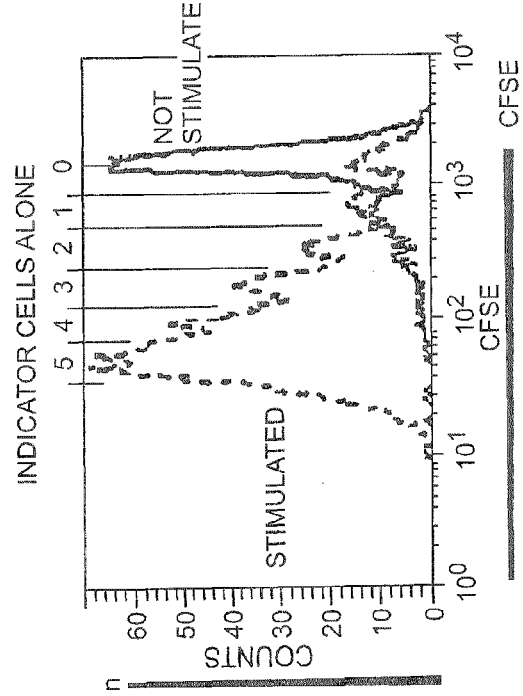
FIG. 22a

USE OF A CD28 BINDING SUBSTANCE FOR MAKING A PHARMACEUTICAL COMPOSITION

STATEMENT OF RELATED APPLICATIONS

This application is a continuation of U.S. patent application Ser. No. 11/585,484, filed Oct. 24, 2006, entitled "Use of a CD28 Binding Substance for Making a Pharmaceutical Composition", which is a continuation of U.S. patent application Ser. No. 10/389,679, filed Mar. 13, 2003, entitled "Use of a CD28 Binding Substance for Making a Pharmaceutical Composition," now abandoned. Both of the prior applications are incorporated herein by reference in their entireties.

FIELD OF THE INVENTION

The invention relates to the use of a CD28 binding substance for making a pharmaceutical composition.
Definitions Monoclonal antibodies (mAbs) are antibodies which are produced by hybrid cell lines (so-called hybridomas) which typically have been generated by fusion of a B cell of animal or human origin producing antibodies with a suitable myeloma tumor cell.

The amino acid sequence of human CD28 is known under accession No. NM_006139.

The C'-D loop of CD28 comprises the amino acids 52 to 66 of the above CD28 sequence (for numbering see also Ostrov, D. A., et al.; Science (2000), 290:816-819). The term C'-D loop will also include in the following any partial sequences therefrom.

A loop or a binding site arranged therein is freely accessible, if for a defined binding partner for the binding site in the loop there is no steric hindrance by the sequences or molecules following to the loop.

Regulatory T cells are CD4+ T cells inhibiting in a mixture with naïve CD4+ T cells the activation thereof. Hereto belong in particular CD4+CD25+ T cells. Another feature of regulatory T cells is, compared to other T cells, a low expression of the high-molecular isoforms of CD45 (human: RA). For regulatory T cells, the constitutive expression of CD152 is typical. CD4+CD8-SP thymocytes are one of the essential sources for regulatory T cells. For a further characterization of regulatory T cells, reference is made to the document K. J. Maloy et al., Nature Immunology, Vol. 2, No. 9, pages 816 ff., 2001.

The induction of regulatory T cells is the increase of the metabolic activity, enlargement of the cell volume, synthesis of immunologically important molecules and beginning of the cell division (proliferation) upon an external stimulation. As a result, after the induction there are more regulatory T cells than before.

Homology is an at least 70%, preferably at least 80%, most preferably at least 90% sequence identity on a protein level, a homologous protein or peptide binding a defined binding partner with at least identical affinity. Deviations in the sequence may be deletions, substitutions, insertions and elongations.

A mimicry compound is a natural or synthetic chemical structure behaving in a defined binding assay as a defined mAb mimicrying the mimicry compound.

The term mAbs comprises, in addition to structures of the conventional Fab/Fc type, also structures exclusively consisting of the Fab fragment. It is also possible to use the variable region only, the fragment of the heavy chains being connected with the fragment of the light chain in a suitable manner, for instance also by means of synthetic bridge molecules, such that the binding regions of the chains form the antibody epitope. The term antibody also comprises (possibly complete) chimeric and humanized antibodies.

Superagonistic stimulation of the proliferation of CD28-specific cells means that no costimulation, i.e. no further binding event in addition to a binding of a mAb or of a mimicry compound to CD28 is necessary for the stimulation or inhibition of the proliferation.

BACKGROUND OF THE INVENTION AND PRIOR ART

For understanding the invention, firstly the following technological background is important. The activation of resting T cells for the proliferation and functional differentiation firstly requires the occupation of two surface structures, so-called receptors: 1. of the antigen receptor having a different specificity from cell to cell and being necessary for the detection of antigens, e.g. viral fission products; and 2. the CD28 molecule expressed on all resting cells with the exception of a sub-group of the human CD8 T cells, said CD28 molecule naturally binding to ligands on the surface of other cells of the immune system. This is called the costimulation of the antigen-specific immune reaction by CD28. In a cell culture, these processes can be imitated by occupation of the antigen receptor and of the CD28 molecule with suitable mAbs. In the classic system of the costimulation, neither the occupation of the antigen receptor nor that of the CD28 molecule alone will lead to the T cell proliferation, the occupation of both receptors is however effective. This observation has been made with T cells of man, mouse and rat.

There are however also known CD28-specific mAbs that can initiate the T cell proliferation without costimulation. Such a superagonistic, i.e. independent from the occupation of the antigen receptor, activation of resting T lymphocytes by CD28-specific mAbs is known in the art from the document Tacke et al., Eur. J. Immunol., 1997, 27:239-247. According thereto, two types of CD28-specific monoclonal antibodies having different functional properties are described: costimulatory mAbs costimulating the activation of resting T cells only with simultaneous occupation of the antigen receptor; and superagonistic mAbs which can activate T lymphocytes of all classes in vitro and in the test animal for proliferation without occupation of the antigen receptor. Both in so far known mAbs originate from an immunization with cells, on which rat CD28 is expressed, and are obtainable by different selections directed to their respective properties.

From the document DE-197 22 888 it is known in the art that superagonistic mAbs are capable to effect an immune deviation TH1 to TH2 and are therefore suitable for use against adjuvant arthritis. TH1 and TH2 cells are CD4-expressing T cells. TH1 cells are also called pro-inflammatory T helper cells and secern the cytokines IL-2, TNF and IFN-γ. TH2 cells support the activation of B cells and secern the cytokines IL-4, IL-5 and IL-10. The differentiation of CD4 T cells from the above functionally different sub-groups is not only controlled by the available cytokines, but it is also modulated by costimulation over CD28. CD28-deficient mice show normal TH1, but reduced TH2-dependent answers and the cytokine profile of TCR transgenic CD4 cells is displaced by CD28 ligation in the direction TH2. On the other hand, a strong TCR signal will prevent CD28-mediated TH2 differentiation.

From the primary literature summarized in the document K. J. Maloy et al., Nature Immunology, vol. 2, No. 9, pages 816 ff., 2001, it is known that regulatory T cells are important for autoimmune reactions. For instance in experimental animal models of the multiple sclerosis, of the type 1 diabetes and of inflammatory intestinal diseases, the capability of these cells to suppress the respective symptoms was shown.

The Guillain-Barré syndrome is an acute autoimmune-inflammatory disease of the peripheral human nervous system. The incidence of GBS is 1 to 2 per 100,000 inhabitants. The chronic form is the chronic demyelinating polyneuropathy (CDP). The incidence of CDP is 10 to 20 per 100,000 inhabitants. mAbs or related substances for the prevention and/or treatment of these diseases are not known.

Technical Object of the Invention

The invention is based on the technical object to specify a pharmaceutical composition, by means of which regulatory T cells can be stimulated and which is particularly suited for the prevention and/or treatment of the multiple sclerosis, type 1 diabetes, inflammatory intestinal diseases, GBS and/or CDP.

BASICS OF THE INVENTION AND PREFERRED EMBODIMENTS

For achieving the above technical object, the invention teaches the use of a CD28-specific superagonistic monoclonal antibody (mAb) or of a mimicry compound thereto, for making a pharmaceutical composition for the induction and/or multiplication of regulatory T cells.

First of all, the invention is based on the finding that by means of superagonistic CD28-specific substances, mAbs or mimicry compounds hereto, CD4+CD25+ T cells can be induced, i.e. the number thereof is, after treatment of an organism with the substance, distinctly higher than in an organism that was not treated or was treated with non-superagonistic substances.

Further, the invention is based on the finding that substances according to the invention obviously are very good drugs for the treatment of the Guillain-Barré syndrome and/or of the chronic demyelinating polyneuropathy and other autoimmune-related diseases. Therefore, the invention further teaches the use for treating these diseases.

Superagonistic CD28-specific substances used according to the invention, i.e. mAbs or mimicry compounds thereto, are those which activate independently from the occupation of the antigen receptor several to all sub-groups of the T lymphocytes.

The substance binds to CD28 or to a partial sequence thereof. The partial sequence may for instance include an amino acid sequence Seq. ID 1 or 2-7 or 17, which lie at least partially in the region of the C'-D loop of CD28. To one of the sequences with val at the 5' end, one or more amino acids of the sequence 8 may be connected in the order defined there. The loop is in the region with the sequence GNYSQQLQVYSKTGF. Mimicry compounds according to the invention can be identified in a screening method, a prospective mimicry compound or a mixture of prospective mimicry compounds being subjected to a binding assay with CD28 or a partial sequence herefrom, in particular the C'-D loop, and substances binding to CD28 or to the partial sequence herefrom being selected, possibly followed by an assay for testing for superagonistic stimulation of several to all sub-groups of the T lymphocytes. In the case of a mixture it will be suitable to perform a deconvolution. Among the selected mimicry compounds so to speak a ranking according to the selectivity and/or affinity may be established, highly affinitive substances being preferred. In addition to or in lieu of such a ranking, a ranking may be performed according to a quantification of the induction of the regulatory T cells or according to the inhibition of the disease for instance in an animal test by using disease models.

An example of a substance used according to the invention is a superagonistic CD28-specific mAb. It can for instance be made by that a non-human mammal is immunized with CD28 or a peptide comprising a partial sequence herefrom, for instance as mentioned above or homologues hereto, cells being taken from the non-human mammal cells and hybridoma cells being produced from the cells, and the thus obtained hybridoma cells being selected such that in their culture supernatant there are mAbs binding to CD28. A humanization can be performed with conventional methods. Suitable mAbs can alternatively be made by selecting B lymphocytes binding to the loop, and by cloning their expressed immunoglobulin genes. An isolation of suitable mAbs from phages libraries is also possible.

In detail, this may be a mAb being obtainable from hybridoma cells, as filed under the DSM numbers DSM ACC2531 (mAb: 9D7 or 9D7G3H11) or DSM ACC2530 (mAb: 5.11A or 5.11A1C2H3). The mAb may comprise one or more of the sequences Seq. ID 9, 11, 13 and/or 15, or one or more of the sequences Seq. ID 10, 12, 14, 16, 18 and/or 19, or sequences being homologous hereto or being (partially) coded thereby. In Seq. ID 13 the nucleic acid sequence of the variable region of the heavy chain of a mAb 5.11A according to the invention is represented. Seq. ID 14 shows the peptide coded thereby. Seq. ID 15 shows the nucleic acid sequence of the variable region of the light chain of this mAb. Seq. ID 16 is the peptide coded hereby. In Seq. ID 9 the nucleic acid sequence of the variable region of the light chain of a mAb 9D7 according to the invention is represented. Seq. ID 10 shows the peptide coded hereby. Seq. ID 11 shows the nucleic acid sequence of the variable region of the heavy chain of this mAb. Seq. ID 12 is the peptide coded hereby. Seq. ID 18 and 19 show the amino acid sequences of the variable region of a humanized mAb 5.11A of the light chain and of the heavy chain, respectively.

The invention finally also relates to treatments, wherein to a person suffering from a disease caused by low regulator T cell counts or high T lymphocytes infiltration in organs or tissues, for instance GBS and/or CDP, a pharmaceutical composition according to the invention is administered in a pharmacologically effective dose and in a galenic preparation suitable for the administration.

Figure 1B:
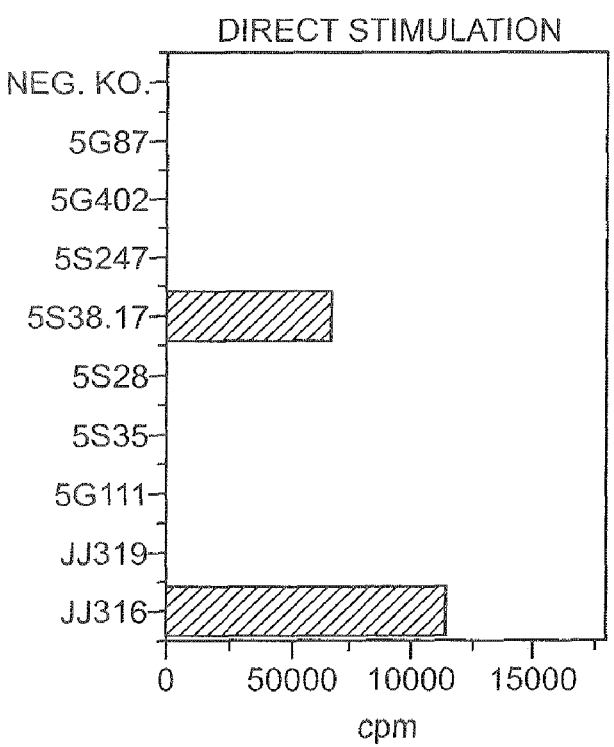
Figure 2:
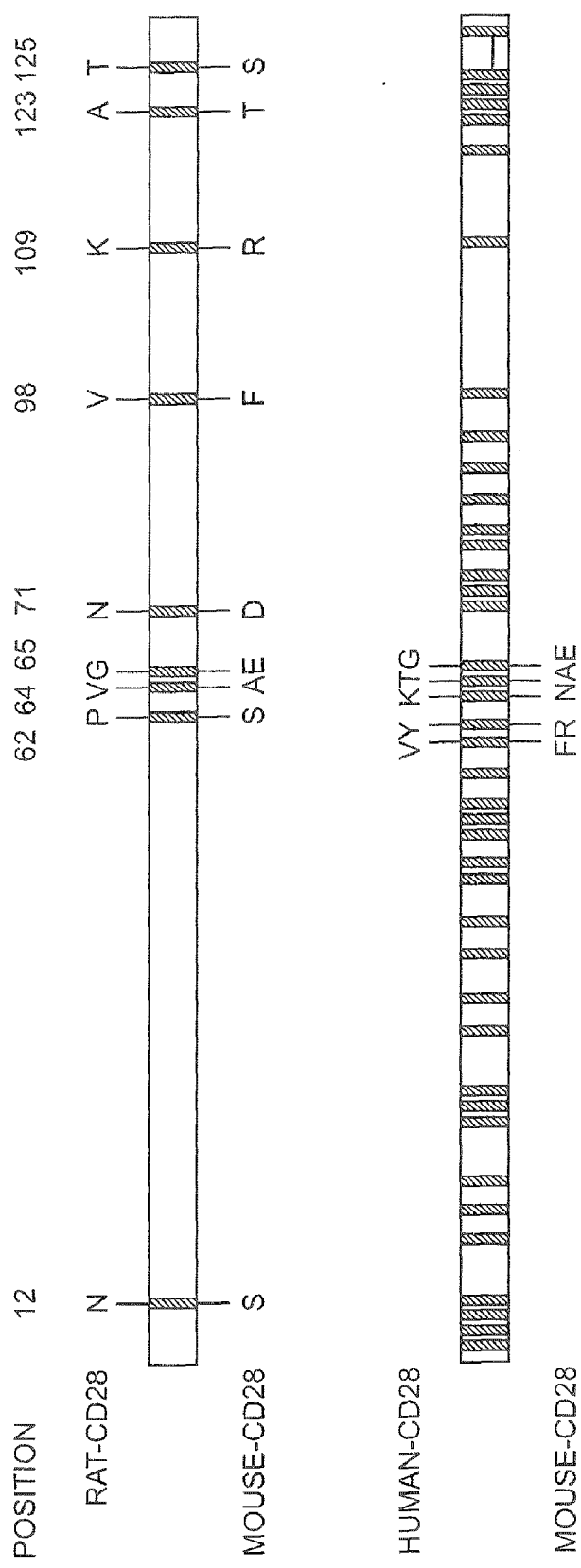
Figure 5:
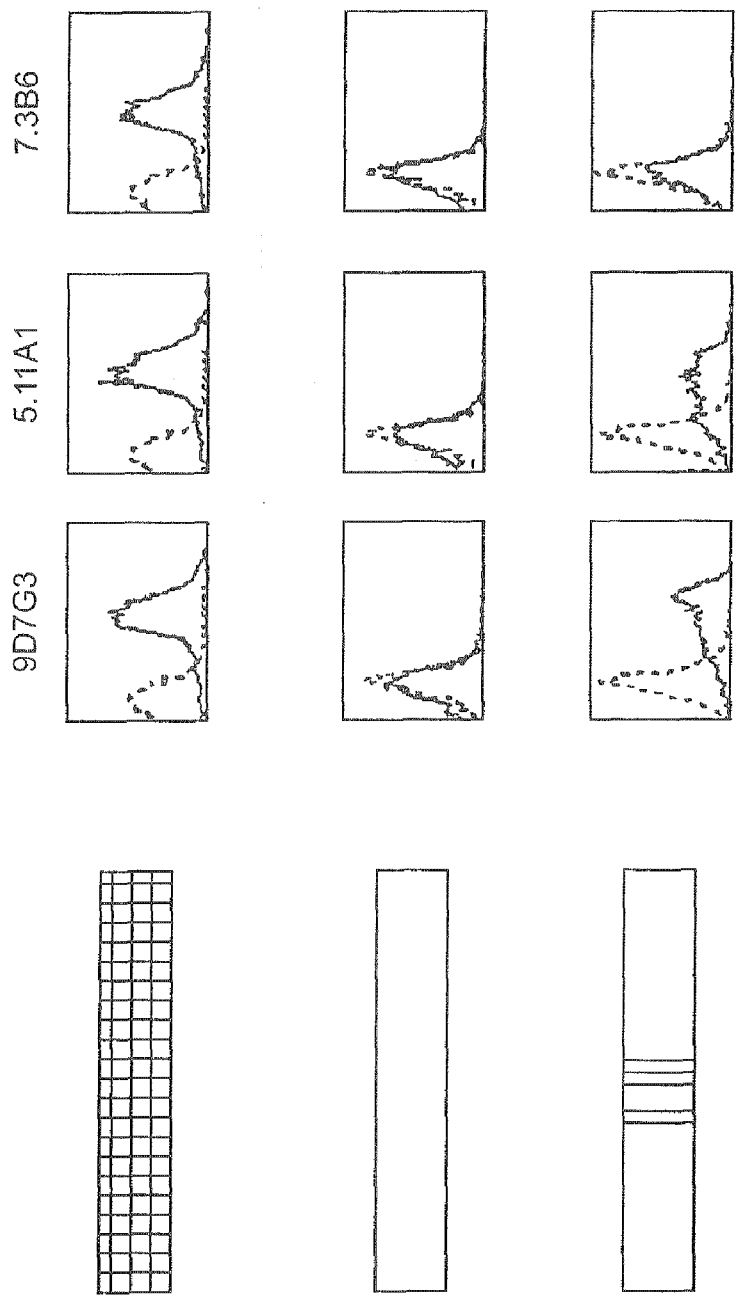
Figure 6:
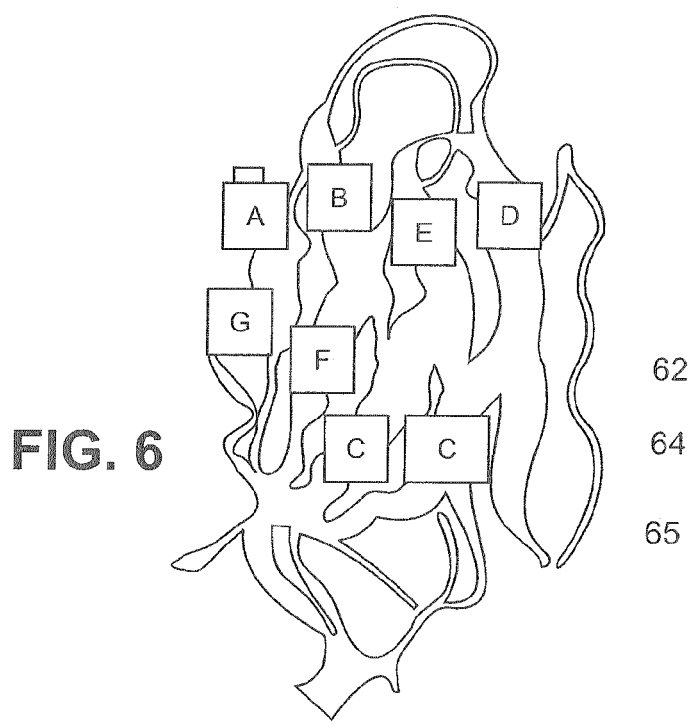

In the following, the invention is explained in more detail, based on examples representing embodiments only. Herein, in FIGS. 1 to 9 and the text sections belonging hereto, methods and results are shown that represent on the one hand target structures for finding suitable substances and that describe on the other hand substances which can be used according to the invention. In FIGS. 10 to 15 are represented results that prove the induction of regulatory T cells by substances used according to the invention. FIGS. 16 to 21 show results hat prove the effect of substances according to the invention in an animal model, the experimental allergic neuritis of the LEW rat (EAN). The EAN is a model for the human GBS and the CDP (also called CIDP or chronic inflammatory demyelinating poly-radiculoneuropathy). There are:

FIG. 1 the stimulation of T lymphocytes of the rat with different CD28-specific mAbs (a: costimulation, b: superagonistic stimulation), FIG. 2 a sequence comparison between mouse, rat and human CD28 in the region of the C'-D loop (in box), FIG. 3 experimental results for localizing the binding site of superagonistic mAb at the CD28 molecule of the rat, FIG. 4 the binding of different human CD28-specific mAbs at CD28 (a) and costimulatory (b) and superagonistic (c) activity of the mAbs of FIG. 4a, FIG. 5 binding tests that show that superagonistic mAbs specifically bind to the C'-D loop, FIG. 6 a three-dimensional representation of CD28 with marking of the C'-D loop, FIG. 7 experiments for the activation of cells by means of mAbs according to the invention, FIG. 8 the representation of the sequences Seq.-ID 9-16 (a-h) and of the humanized variable domain of the antibody 5.11A (light chain: VLC5.11, i; heavy chain: VHC5.11, j), Seq.-ID 18-19, FIG. 9 the frequency of the CD4+CD25+ cells in the total population of the CD4 cells of a rat, in comparison to after a treatment with a superagonistic CD28-specific mAb and a costimulatory mAb, FIG. 10 the phenotypic characterization of CD4+CD25+ cells induced by superagonistic CD28-specific mAbs and the comparison with CD4+CD25– and CD4+CD25+ cells from untreated control animals, FIG. 11 the induction of the proliferation of CD4+CD25+ cells by superagonistic CD28-specific mAbs in a cell culture, FIG. 12 another phenotype of the CD4+CD25+ cells obtained according to FIG. 11, FIG. 13 the inhibitory function of the regulatory T cells, FIG. 14 the experiments according to FIG. 11 with human T cells and the use of superagonistic human-CD28-specific mAbs, FIG. 15 the course of the active EAN disease under treatment with superagonistic CD28-specific mAbs in comparison with costimulatory mAbs, FIG. 16 the effect against ENA by administration of superagonistic CD28-specific mAbs before the immunization with the autoantigen inducing EAN, FIG. 17 the treatment according to FIG. 15, however with a different treatment plan, FIG. 18 the treatment according to FIG. 15, however for the case of the passive or adoptive transfer EAN, FIG. 19 the sorting of human CD4+ cells in CD4+ CD25+++ and CD4+CD25– cells, FIG. 20 the growth curves of T cells expanded by monoclonal antibodies and IL-2 according to the invention of FIG. 19 (sorted), FIG. 21 the CTLA-4 expression of the expanded T cells of FIG. 20, and FIG. 22 the functional analysis of the expanded T cells of FIG. 20 by means of a suppression assay, A: proliferation of the indicator cells without and with stimulation (CD3/anti CD28), B: suppression of the proliferation of the indicator cells in presence of expanded CD4+CD25+++ cells.

FIG. 1 shows the stimulation of freshly isolated T lymphocytes of the rat in the form of a 3H thymidine incorporation. The method corresponds to the one described in the document WO98/54225, to which here and in the following explicitly reference is made and its disclosure contents are herewith incorporated in the present text. In FIG. 1a is shown the costimulation, i.e. T cell receptor (TCR) specific mAbs were bound to the plastic surface in all wells. Because of lacking costimulation, the negative control (uppermost bar) does not show any incorporation. Costimulation is then given by the addition of CD28-specific mAbs in a dissolved form. The complete shown range of CD28-specific mAbs was used. This series of different CD28-specific mAbs originates from an approach of the immunization and preparation of hybridoma cell lines described in WO98/54225. These are culture supernatants containing enough CD28-specific mAbs for a saturating binding to $2 \cdot 10^5$ T cells. From FIG. 1a can be taken that all of these mAbs are able to activate in a costimulating manner, i.e. to excite the thymidine incorporation in presence of the anti-TCR mAbs. In FIG. 1b is shown the stimulation in absence of TCR-specific mAbs. This experiment, too, was performed as described in WO98/54225. It can be seen that only two mAbs are able to stimulate the T lymphocytes in absence of a TCR signal. These mAbs have thus a superagonistic activity.

Further, it was investigated whether costimulatory and superagonistic CD28-specific mAbs bind to different regions of the CD28 molecule. The mAbs were prepared by immunization of mice with CD28 of the rat; as expected, they all do not react with mouse CD28 (not shown). Since the mAbs can thus detect only such regions of the rat CD28 molecule which are different from the mouse, first a sequence comparison between the CD28 of the mouse and of the rat was made (see FIG. 2, upper section). The differences between the two species are highlighted. For identifying the amino acids, a one-letter code was used. As prototypes for a conventional rat CD28-specific mAb JJ319 was used, for a superagonistic mAb JJ316 was used (see WO98/54225).

In FIG. 3 is shown the mapping of the binding. Expression plasmids were constructed, wherein a part of the extracellular domain of CD28 originates from the mouse, another one from the rat. This is symbolically shown by bars or lines; on the right hand thereof is shown the binding of the mAbs JJ316 and JJ319 to mouse fibroblasts (L929 cells) transfected with these expression plasmids. In the first two lines of FIG. 3 (m/r and r/m 1-37) the binding of the two antibodies to the "right-hand" half of the sequence is mapped. Both bind, when the latter originates from the rat. In the reversed construct (rm CD28 1-37, left hand rat, right hand mouse) there is no binding. In the third line (m/r CD28 1-66) it is shown that JJ316 does not bind anymore, whereas the still present part of the rat sequences ("right-hand") sill suffices for the detection by JJ319. According thereto, the two mAbs detect different epitopes on the CD28 molecule, and the binding of the superagonist JJ316 is therefore to be searched in the region which originated in the construct of the first line, not however in the construct of the third line from the rat. A clear candidate here-for is the region in the box in FIG. 2.

In lines 4 and 5 of FIG. 3, therefore firstly two and then three amino acids in this region of the mouse CD28 molecule were modified such that they now represent the rat sequence. By this "transplantation" of three amino acids only, the binding capability for mAb JJ316, not however (as expected) that of JJ319 could be transferred. In Table 1 are summarized the binding data for the complete range of CD28-specific mAbs. There results a clear correlation: the two mAbs which function even without TCR stimulation (superagonists) detect said epitope (in box in FIG. 2), the conventional mAbs (only costimulatory) however do not. A costimulatory mAb (5S35) detects the epitope in box very weakly and binds very strongly to the "conventional" epitope.

The next two figures deal with superagonistic human-specific mAbs. These, too, were prepared in mice, thus do not react with the CD28 molecule of the mouse. The mice were immunized with human-CD28-transfected A20/J mouse B lymphoma cells (see WO98/54225) and in addition boostered prior to the fusion with commercially available human-CD28 FC fusion protein (bought from R and D Systems). In a series of fusion experiments, from several thousand cell lines, approx. 20 were identified producing human-CD28-specific mAbs (binding to mouse L929 cells expressing human-CD28, but not to untransfected L929 cells), analogously to the screen in document WO98/54225. Two of these showed the searched superagonistic activity (9D7 and 5.11A), whereas all new mAbs have the conventional costimulatory activity. In the following, in particular the two superagonistic mAbs are described. As an example for a conventional human-CD28-specific mAb, the also newly generated mAb 7.3B6 was used.

FIG. 4a shows that the used preparations of the three new mAbs bind comparatively well and also with a comparative titer to human T lymphocytes. It is shown an experiment wherein freshly isolated mononuclear cells from the human blood (so-called PBMC) firstly were treated with different dilution steps of the used mAbs on ice; then they were washed, and the bound mAb was made visible by a secondary antibody marked with a fluorescence dye, said antibody specifically detecting the bound mouse mAb. By the use of another mAb which detects human CD4 cells and to which was bound a second fluorescence dye, the binding of the titrated mAbs could be determined by electronic gating selectively for the CD4 T lymphocytes. "MFI" is the median fluorescence intensity being a measure for the amount of the bound CD28-specific mAb. The concentrations are 1:3 dilutions of a standardized original preparation. It is fully normal that in this test the highest concentration provides a weaker signal than the following titration steps; this has to do with the avidity (bivalent binding) of mAbs and does not play a role in the contexts discussed here.

FIGS. 4b and c compare the capabilities of superagonistic human-CD28-specific mAbs to those of conventional CD28-specific mAbs—in presence and in absence of a TCR signal—to stimulate freshly isolated human T cells to growth. Again a 3H thymidine incorporation is shown, as described before for the rat. For FIG. 4b, the wells were coated with a mAb reacting with the human TCR/CD3 complex. Thus costimulation was measured. It can be seen that the proliferation does not occur without a costimulation with one of the mAbs (negative control), all three antibodies are however able to stimulate the cell division. For FIG. 4c, the procedure took place in absence of a TCR/CD3-specific mAb. Only the antibodies 9D7 and 5.11A could stimulate in a superagonistic manner.

After the epitope for superagonistic mAbs for the rat is defined, and two new superagonistic mAbs with specificity for human CD28 have been isolated, it was verified whether these mAbs bind to the corresponding position of the human CD28 molecule. As can be seen in FIG. 2, the CD28 molecules of mouse and man differ in numerous positions. On the basis of the mapping of the superagonistic epitope for the rat, it was therefore directly verified whether the binding site for the superagonistic epitope on human CD28 to the CD28 molecule of the mouse can be achieved by a "transplantation" of the five amino acids of this homologous region. The results are shown in FIG. 5. With the background of the homogeneously represented mouse sequence for the extracellular domain of the CD28 molecule (center), the exchanged (mouse to human) amino acid positions are shown as lines (bottom). The numbers at the sides in addition indicate the individual positions and mutations (F60V means for instance that at position 60 the phenylalanine of the mouse was replaced by a valine of the human sequence). Moreover, the binding of the three investigated mAbs is represented. As the figure shows, all three mAbs do detect human CD28, however only the two mAbs 9D7 and 5.11A react with the mouse CD28 molecule to which were transplanted the five amino acids of the human CD28 at the decisive position. In view of the variety of differences, this specific preparation of the reactivity is surprising and confirms to a full extent the finding derived from the experiments with rat CD28, namely that superagonistic mAbs must bind to a defined, namely this position of the molecule.

FIG. 6 is a three-dimensional model of the CD28 molecule. The newly defined binding region is highlighted. It corresponds to the sequence in the box in FIG. 2. The extracellular domain of CD28 structurally belongs to the immunoglobulin superfamily being characterized by two superimposed β-pleated sheets as a basic structure. The labeling of these bands follows a pattern given in the literature. It is important for the representation shown here that the region identified as an epitope for superagonistic CD28-specific mAbs in rat and mouse are designated "C'-D loop". Thus it was shown that mAbs with specificity for the C'-D loop of the CD28 molecule have superagonistic activity, that is, in the meaning of the document WO98/54225, can be used for the activation of T lymphocytes. The superagonistic activity of C'-D loop-specific mAbs in rat and man shows that not the sequence of the epitope, but its position or shape is important.

Figure 7A:
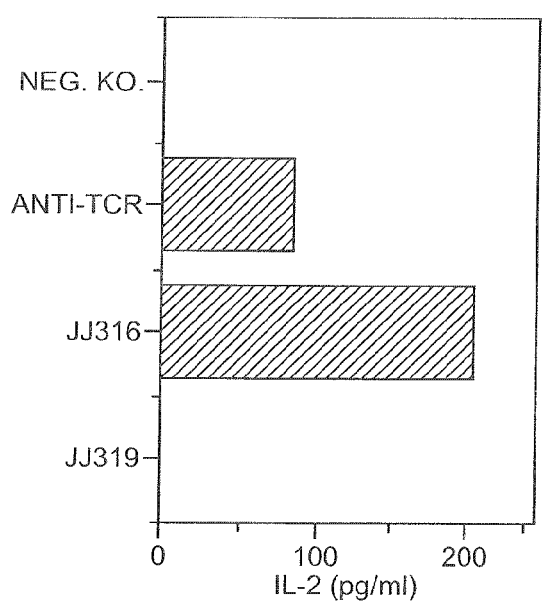
Figure 7B:
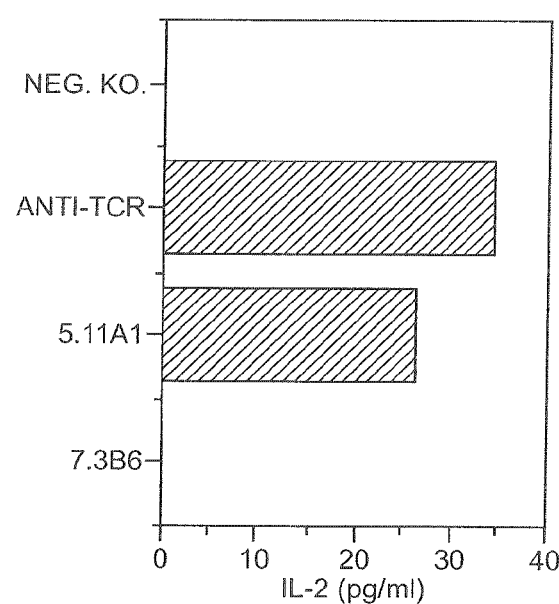

In the experiments of FIG. 7, it was investigated whether mAbs do not only bind (see FIGS. 3 and 5), but whether there is really an activation. For this purpose, T tumor cells of the mouse, BW, were transfected either with the construct of FIG. 3, line 5 (rat C'-D loop transfer) or with the construct of FIG. 5, line 3 (human C'-D loop). The activation of these cells is not measured by cell division (they proliferate anyway), but by the production of the cytokine IL-2. FIG. 7 shows that without stimulation there is no IL-2 production (negative control). The stimulation with a T cell receptor-specific mAb induces IL-2 production (positive control). FIG. 7a shows the results when using the superagonistic mAb JJ316 of the rat, whereas FIG. 7b shows the results for the human C'-D loop-specific mAb 5.11A. In either case the respective cell lines are stimulated to IL-2 production. As expected, the stimulation did however not take place by means of "conventional" CD28-specific mAbs, since they do not only bind to the C'-D loop, but cannot detect at all the construct, because they are specific for the rat or human-specific sequences which are not included in the construct.

In FIG. 9 are shown dot plots, wherein every measured cell is represented by a dot. The phenotypic characterization of the regulatory T cells takes place by the combination of the cell surface molecules CD4 and CD25. For this purpose, the cell suspensions were incubated with correspondingly fluorescence dye marked monoclonal antibodies against CD4 and CD25, washed and examined in a flow cytophotometer for the binding of these antibodies. The shown results were obtained three days after IP injection of a costimulatory (FIG. 9a, JJ319) or superagonistic CD28-specific mAb (FIG. 9b, JJ316). In the case of JJ319, approx. 7% of the CD4 T cells are also CD25− positive(4/(50+4)), which corresponds to not shown results in untreated animals. However, after treatment with JJ316, approx. 20% are CD4+CD25+ (10/(10+40)). Further, the level of the CD25 expression is by far higher than in the control animal. Such a high level is characteristic for regulatory T cells.

FIG. 10 shows a phenotypic characterization in a representation as a histogram. In FIGS. 10a to 10c, the marker CD45RC was detected, a high-molecular isoform of the CD45 molecule being expressed strongly on naïve CD4 T cells, however weakly on stimulated CD4 T cells. A weak expression is typical for regulatory T cells. FIG. 10a shows that most CD4+C25− cells from untreated animals strongly express CD45RC. However, in the case of CD4+CD25+ cells from untreated animals, a strong expression takes place in a clear minority of all cells (FIG. 10b). In the case of the treatment with the superagonistic CD28-specific mAb (FIG. 10c), the downward regulation of CD45CD45RC is even more distinct than in the case of FIG. 10b. In the case of FIGS. 10d to 10e, the CD152 (CTLA-4) constitutively expressed by regulatory T cells is detected by staining. This staining must be performed, because of the intracellular localization of CD152, after permeabilization of fixed cells, and is therefore provided with an unspecific background. For verifying this, a so-called isotype control was performed, i.e. an intracellular staining with a mAb of the same immunoglobulin class, which however cannot detect anything specifically. The specific CD152 proof is obtained by a displacement of the CD152 histogram with regard to the isotype control histogram. In FIG. 10d cannot be seen a displacement and thus no CD152 expression in the CD4+CD25− cells. In the untreated CD4+CD25+ cells there is a weak displacement (FIG. 10e) and in the JJ316 (superagonistic CD28-specific mAb) treated cells there is a stronger displacement, in agreement with the results of FIGS. 10a to 10c.

As a result, it is phenotypically shown, with FIGS. 9 and 10, how regulatory cells can be identified, and that superagonistic CD28-specific mAbs preferentially multiply or induce in vivo regulatory T cells.

Figure 11B:
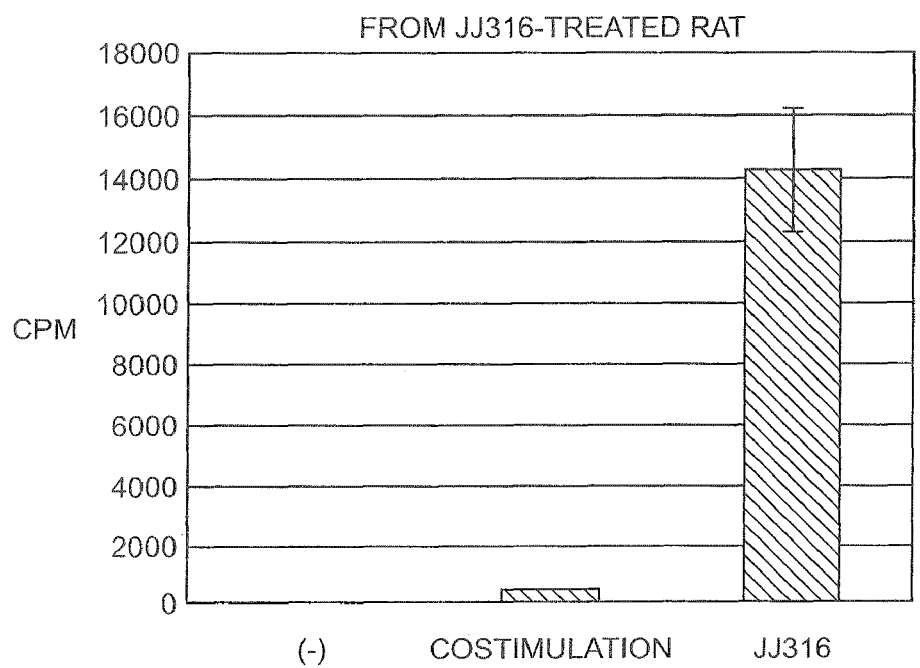
Figure 12:
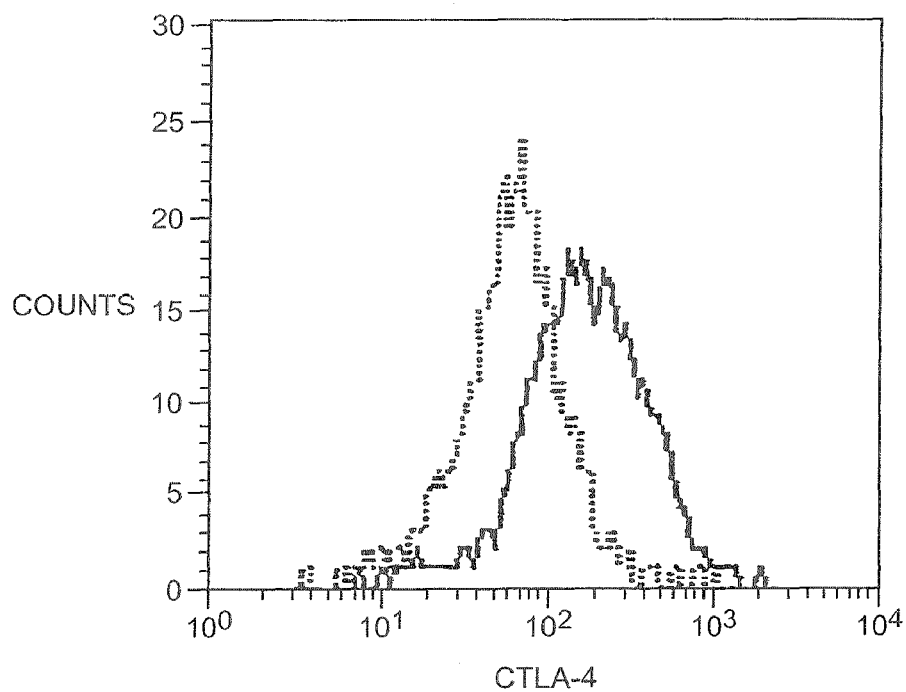

In FIG. 11, CD4+CD25+ cells are isolated by electronic cell sorting either from untreated rats (FIG. 11a) or from rats treated with JJ316 (FIG. 11b) and cultivated in 96 well plates according to the state of the art. The cell multiplication was measured by 3H thymidine incorporation between day 2 and 3 of the cultivation. "(−)" means no stimulation, costimulation means stimulation with a non-superagonistic CD28-specific mAb (JJ319) and with the TCR-specific R73, and JJ316 shows the superagonistic stimulation. FIG. 11a as well as 11b show that regulatory cells do not react well upon costimulation, however well upon stimulation with a superagonistic CD28-specific mAb. Stimulation with mAbs used according to the invention shows also in a cell culture a considerable multiplication of regulatory T cells.

FIG. 13 shows a representation according to FIG. 10f, however after in vitro stimulation with superagonistic CD28-specific mAbs (JJ316). An even stronger detectable CD152 expression can be seen.

Figure 13A:
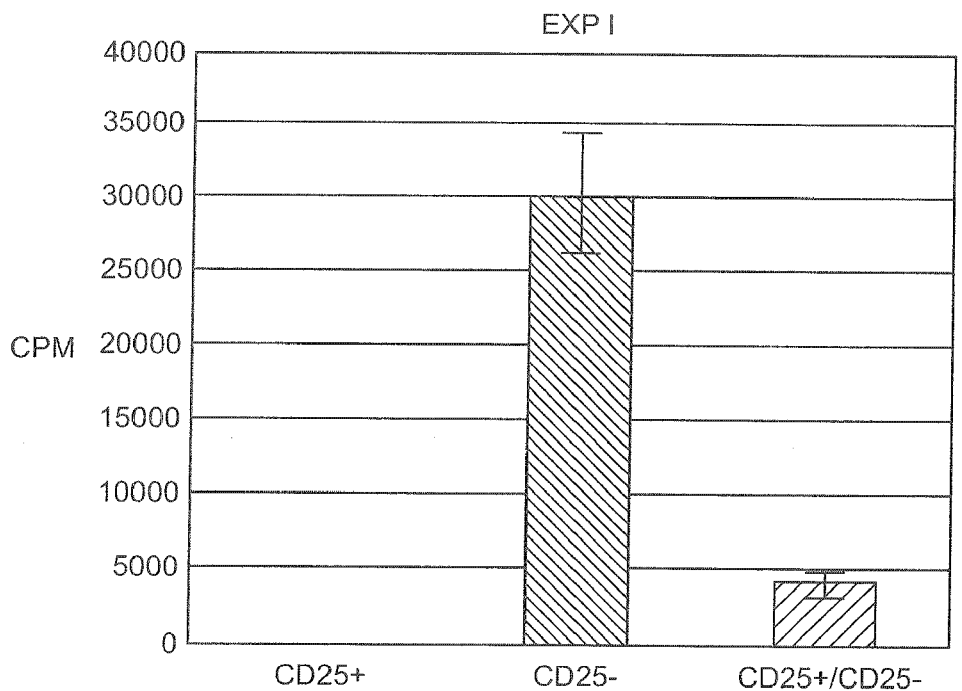
Figure 13B:
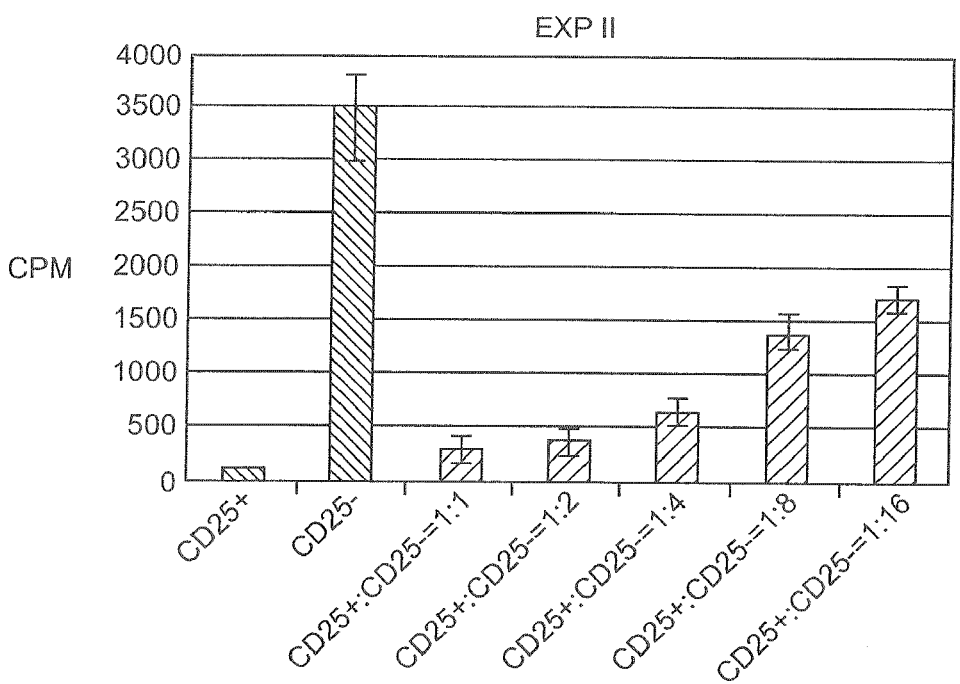

In FIG. 13 is shown the inhibitory function of regulatory T cells on Cd4+CD25− T cells serving as indicator cells for the suppression effect. As a stimulus for the CD4+CD25− T cells, costimulation (R73+JJ319) was used. The 3H thymidine incorporation between day 2 and 3 of the cultivation was measured. CD25+ means electronically sorted CD4+CD25+ T cells from animals treated three days before with superagonistic CD28-specific mAbs (JJ316). CD25− represents the indicator cells. CD25+/CD25− means in FIG. 13a that both cell populations were mixed with one another in identical parts. It can be seen that upon costimulation the CD25+ cells do not react with proliferation. Further, the proliferation of indicator cells is in addition suppressed. In FIG. 13b is represented a titration of the regulatory T cells by a mixture with indicator cells in different quantities. It can be seen that even with a ratio of regulatory to indicator cells of 1:16, suppression can still be observed. This shows the high effectivity of the regulatory cells stimulated with mAbs used according to the invention.

Figure 14:
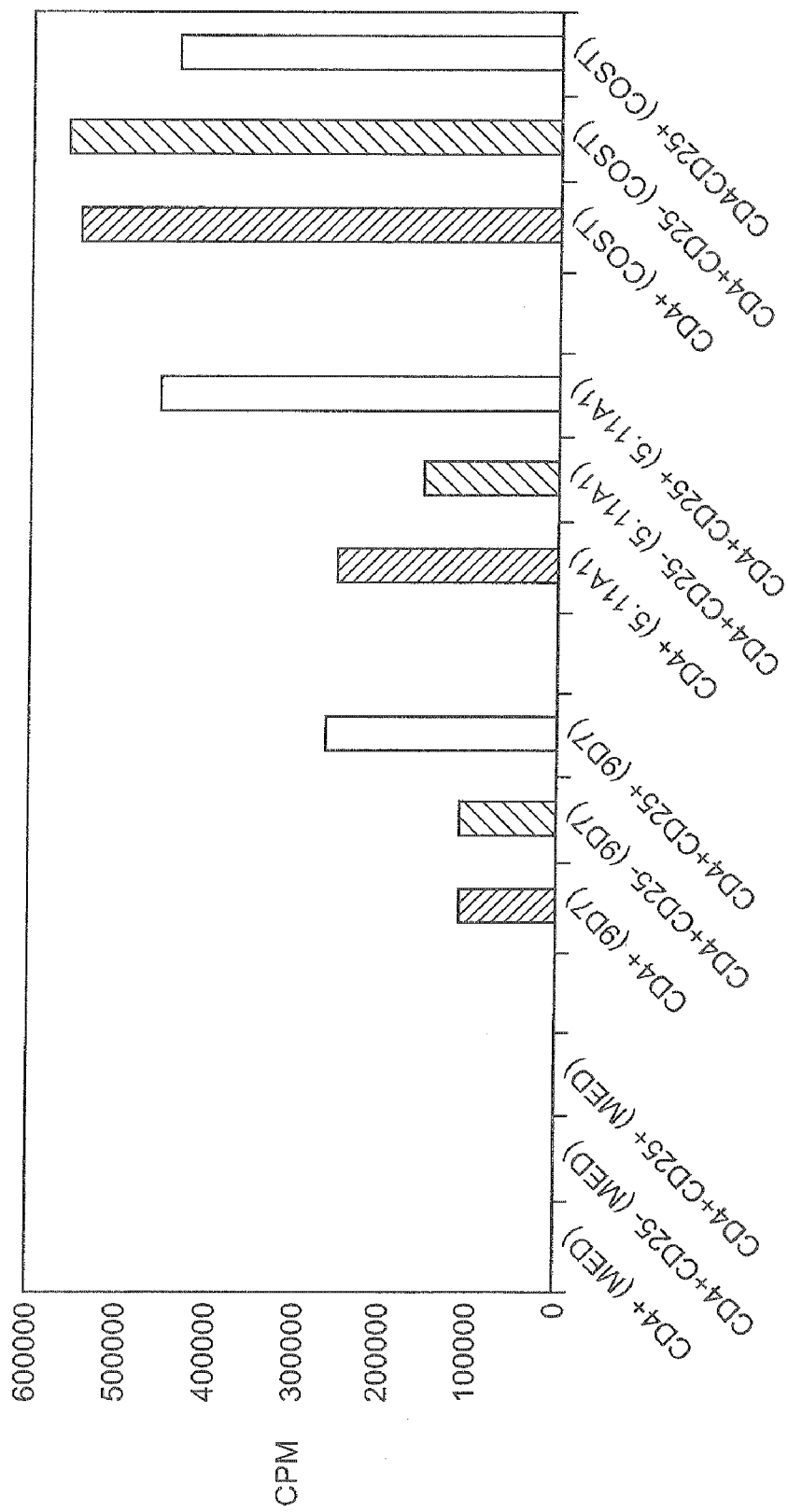

FIG. 14 shows a comparison of the reactions of human CD4+CD25− T cells (naïve cells) to CD4+CD25+ T cells (regulatory cells) in response to costimulation (anti-CD3+ conventional anti-CD28 mAb) or to human-specific superagonistic CD28-specific mAbs (9D7 and 5.11A). The experiments correspond to those described above for the rat. Beginning at the left-hand side, the first three groups show unstimulated controls (no 3H thymidine incorporation). These are all CD4+ T cells, then the CD25− fraction gained by sorting and finally the CD25+ fraction gained by sorting. "med" means medium. Then follow two groups wherein a superagonistic stimulation was made (9D7 and 5.11A). It can be seen that the regulatory T cells react in a better way on the stimulation with superagonistic CD28-specific mAbs, compared to the total population of the CD4+ cells and their CD25− fraction. The last group of three shows the results of the conventional costimulation. Here, however, the reaction of the unseparated T cells and of the CD25− fraction is rather better.

As a result, it is proven for rat T cells as well as in the human system that superagonistic CD28-specific mAbs induce or multiply regulatory T cells in a better way than conventional costimulation. Further, it is proven that this can also be verified in the intact organism.

Figure 15A:
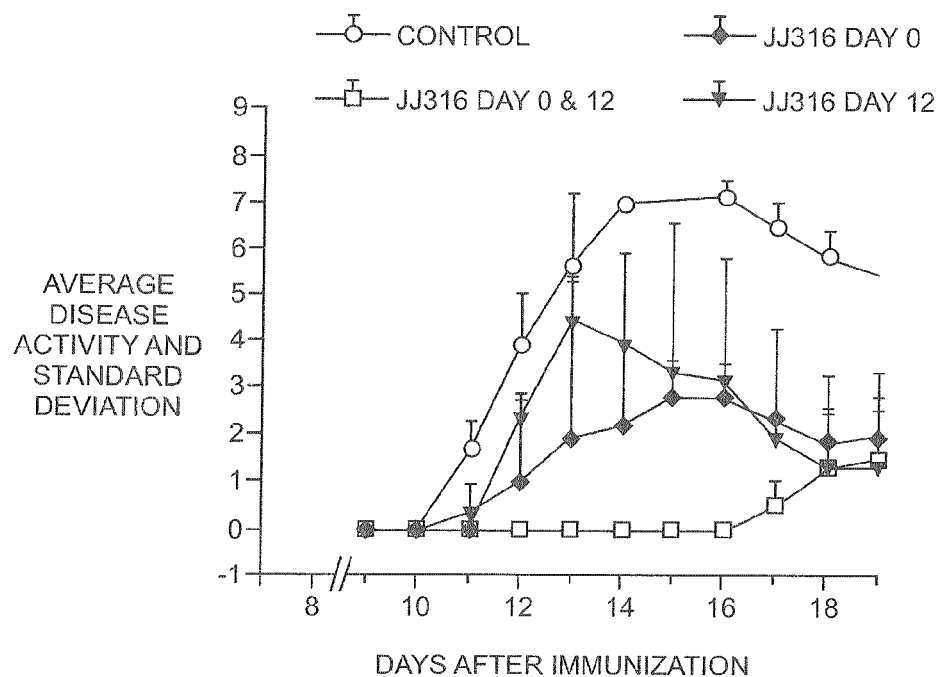
Figure 15B:
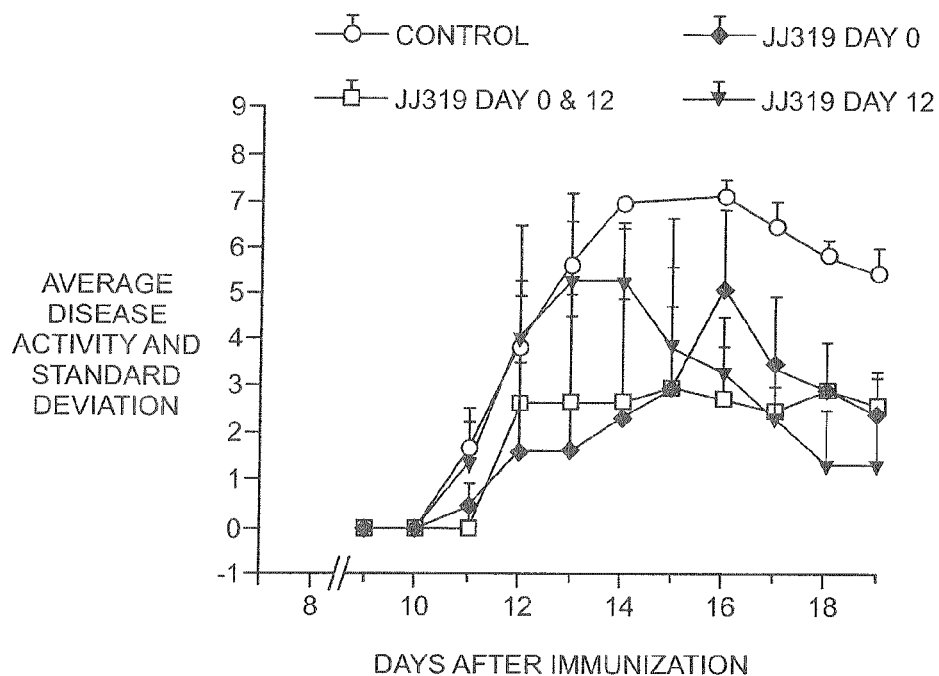

In FIG. 15 is represented the course of the active EAN disease under treatment with various mAbs. 7-8 weeks old female LEW rats (obtainable from Charles River Laboratories, Sulzfeld, Germany) were used. The animals were immunized with a synthetic peptide corresponding to a part of the myelin protein P2 wrapping peripheral nerve fibers (amino acids 53-78 of the bovine P2 protein, 50 µl of a 0.5 mg/ml solution, inoculation in the foot balls). After approx. 10 days a progressive paralysis develops which can be quantified according to a standardized scoring (King et al., Exp. Neurol., 87:9-19 (1985)). FIG. 15a shows a preparative therapy with superagonistic CD28-specific mAbs (JJ316) and FIG. 15b a treatment with conventional mAbs (JJ319). The application took place in 1 mg/animal doses IP either on the day of the P2 immunization (D0), at day 12 (D12), i.e. after beginning of the symptoms, or on both days. The various groups comprises 3 to 6 animals. A comparison of FIGS. 15a and 15b shows that the treatment with superagonistic CD28-specific is distinctly more effective than the treatment with conventional mAbs.

Figure 16:
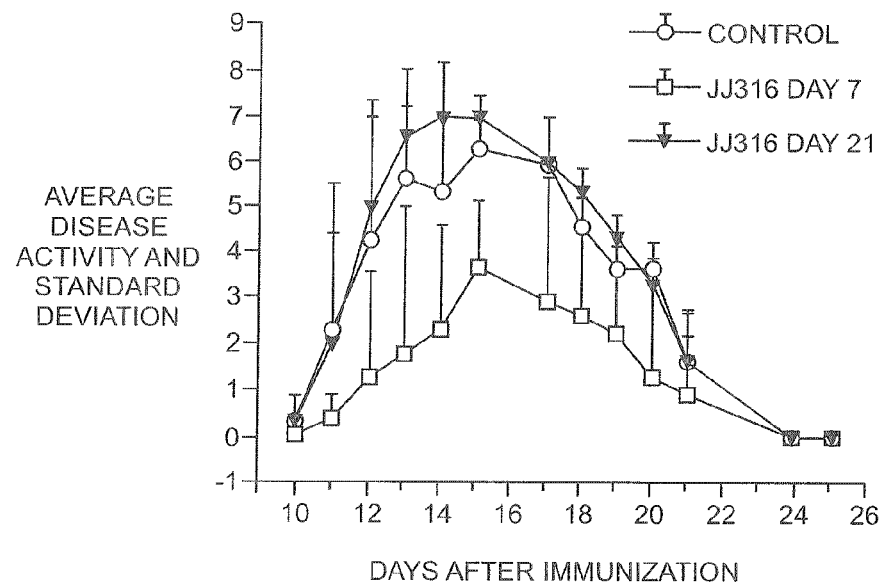

FIG. 16 shows the results according to FIG. 15, however with a prophylactic treatment. d-7 is a treatment 7 days before the immunization, d-21 21 days before the immunization. It can be seen that a resistant state can be achieved by multiplication of regulatory T cells with a treatment within one week before the immunization, not however with a treatment 3 weeks before the immunization.

Figure 17A:
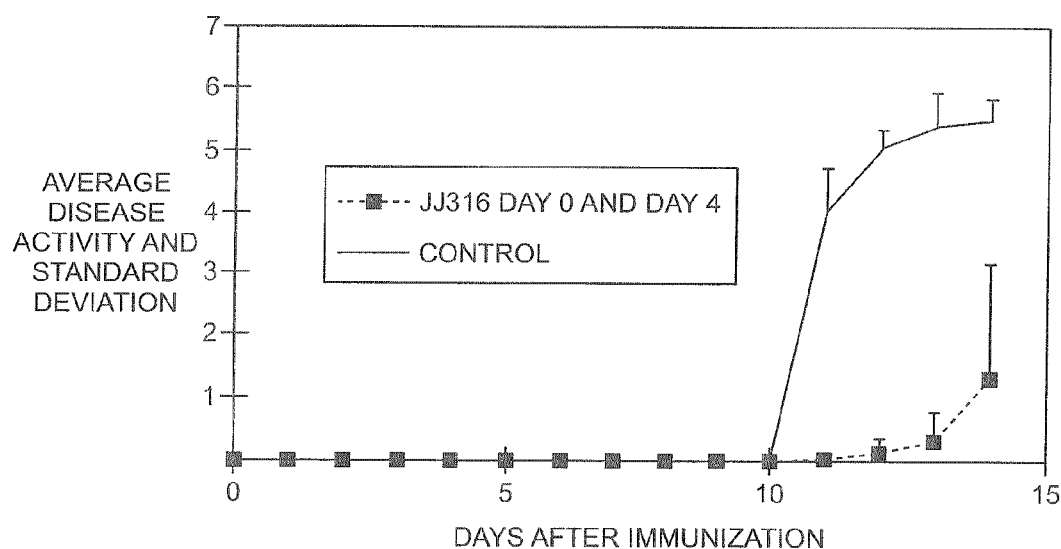
Figure 17B:
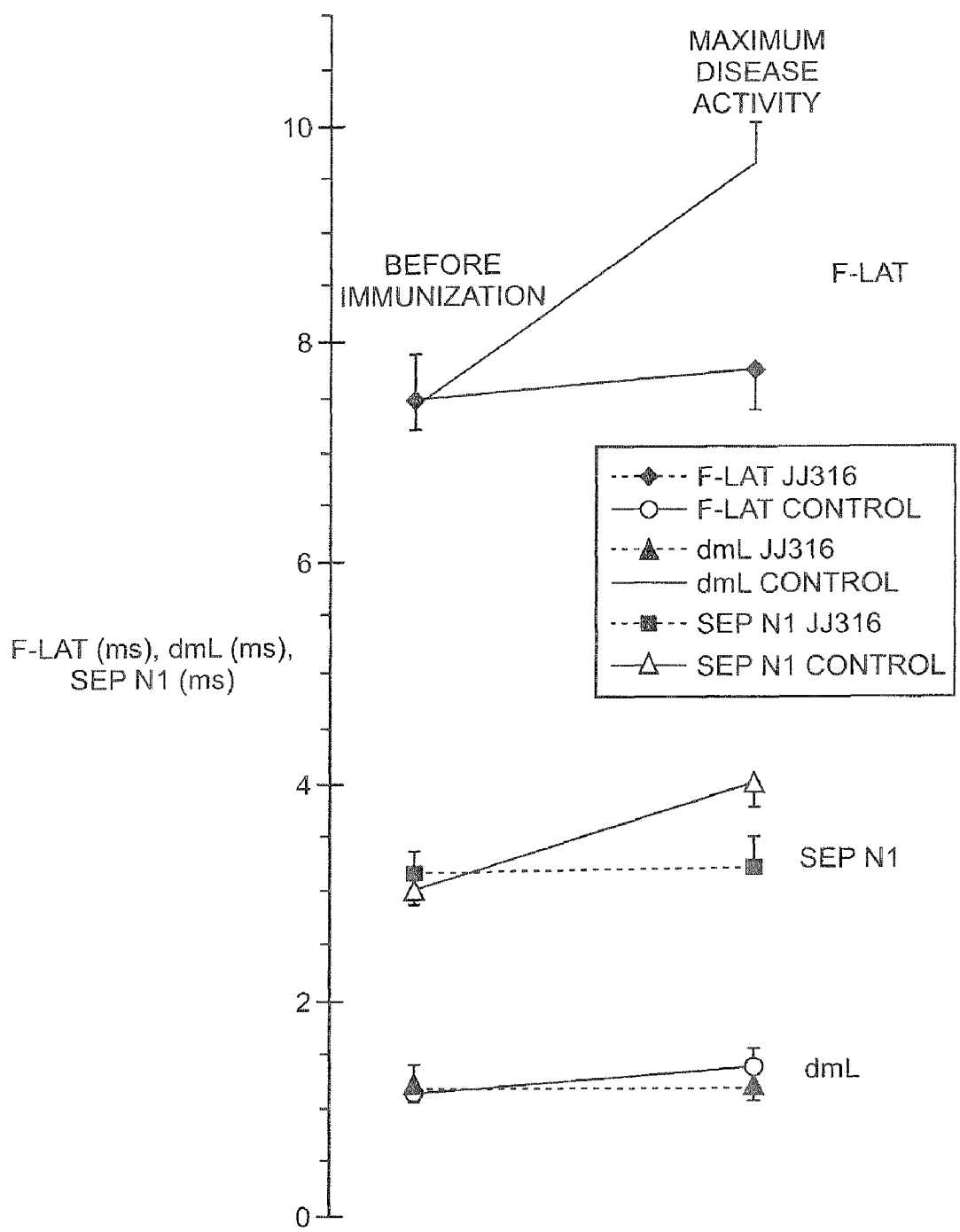
Figure 17C:
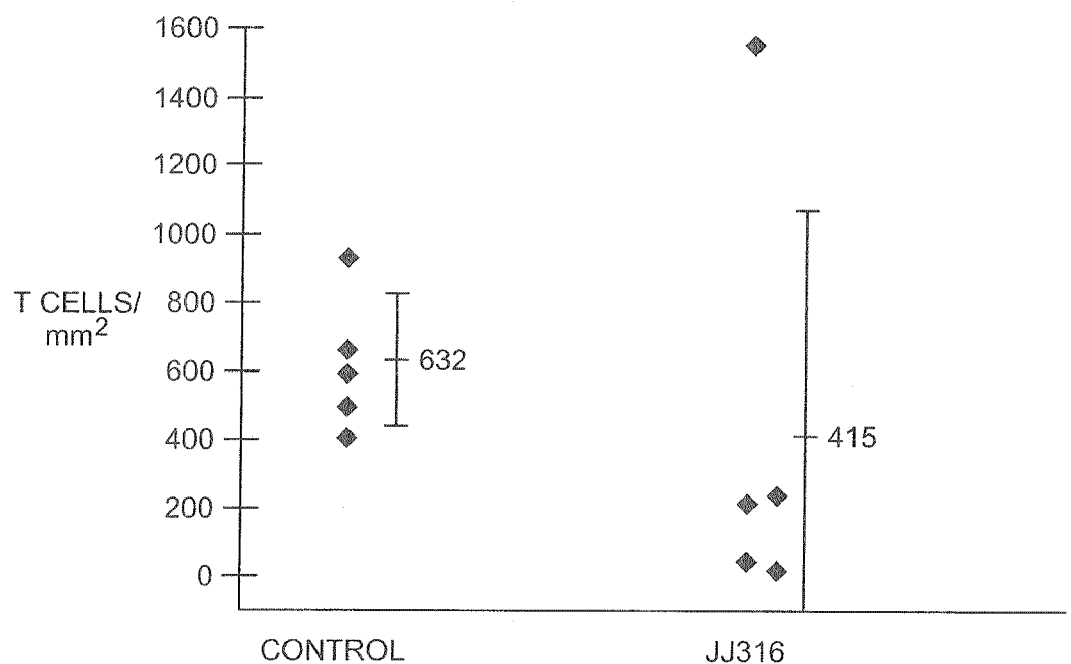

FIG. 17 is based on an approach identical to FIG. 15, however treatment with JJ316 at day 0 and 4. FIG. 17a shows the course of the disease corresponding to the representation of FIG. 15a. FIG. 17b shows electro-physical properties, namely speed of the stimulus transmission as a direct clinical parameter for the damage of the sciatic nerve. The measurements were performed according to the documents Adlkofer et al., Nat. Genet., 11:274-280 (1995) and Heininger et al., Ann. Neurol., 19:44-49 (1986). The pathological results can be seen by means of control groups in particular in the extension of the N1 and F latencies (see days 0 and 12, open symbols). In contrast, the latencies in the case of the animals treated with superagonistic CD28-specific mAbs (JJ316) remain nearly unchanged between day 0 and day 12 (full symbols).

Not shown are supplementing examinations with a histological proof of the T cell infiltration in thin layers of the nerves. The detection of the cells took place with a mAb being suitable for this technology, namely B115 and coloration of the T lymphocytes. The cell nuclei were counter-colored in a different color. In comparative experiments it was found that in the not treated control group, a higher number of T cells were infiltrated than in the group treated with a superagonistic CD28-specific mAb (JJ316), which indicates a suppression by regulatory T cells by using mAbs according to the invention.

Further experiments are not shown wherein the isolating myelin sheaths were colored. The treatment with superagonistic CD28-specific mAbs showed a healthy picture, whereas the control group showed demyelinization, i.e. destruction of the isolating sheaths.

Figure 18A:
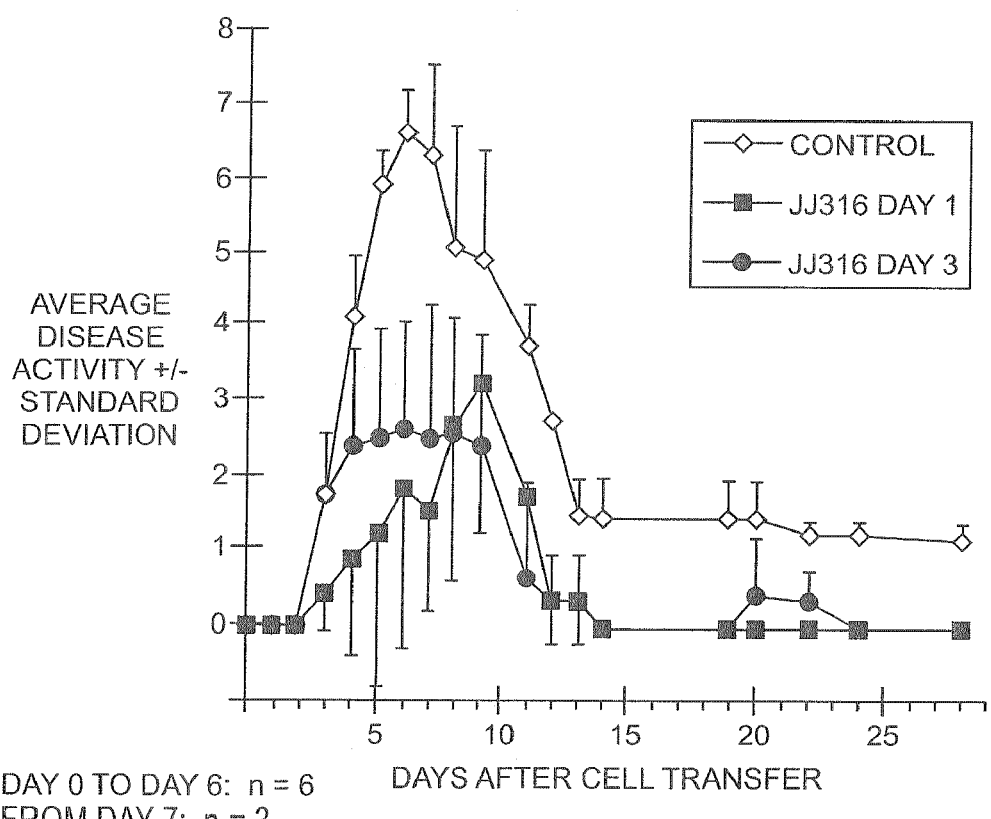
Figure 18B:
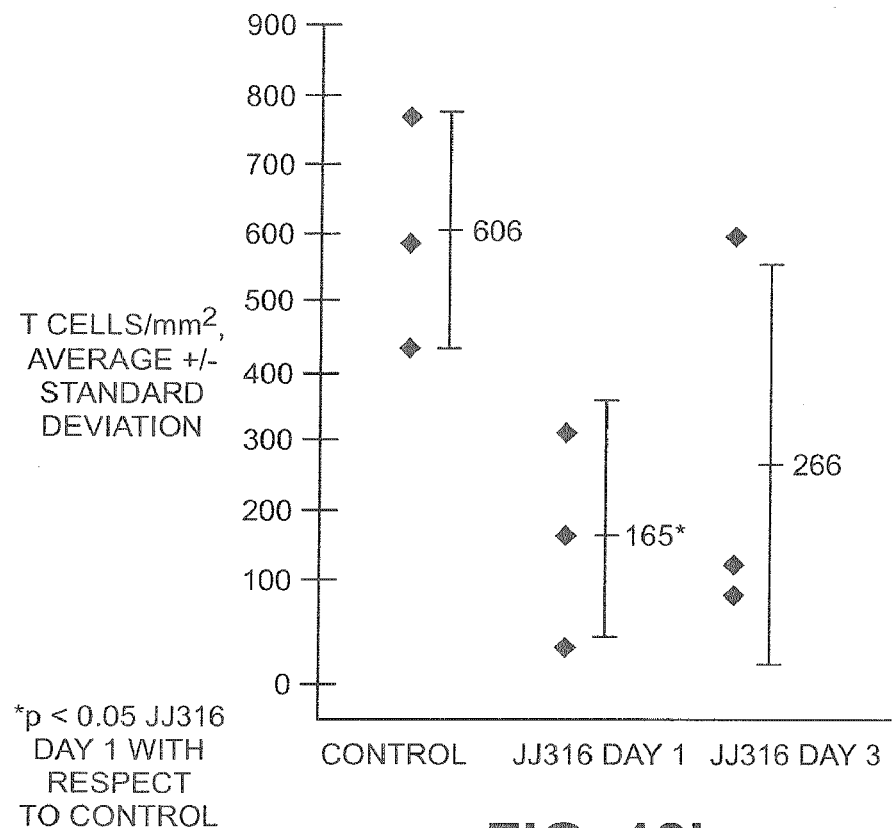
Figure 21:
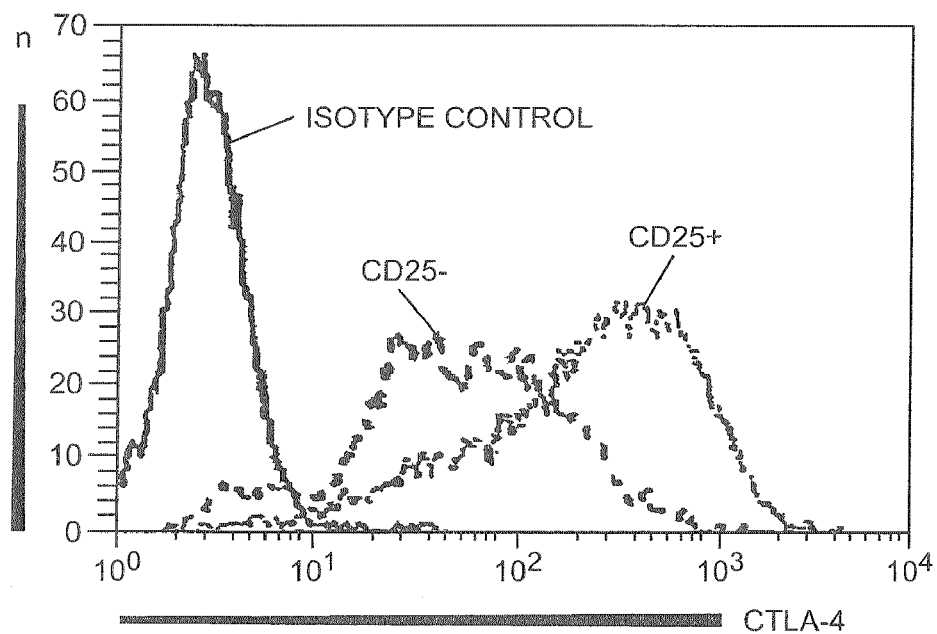
Figure 19:
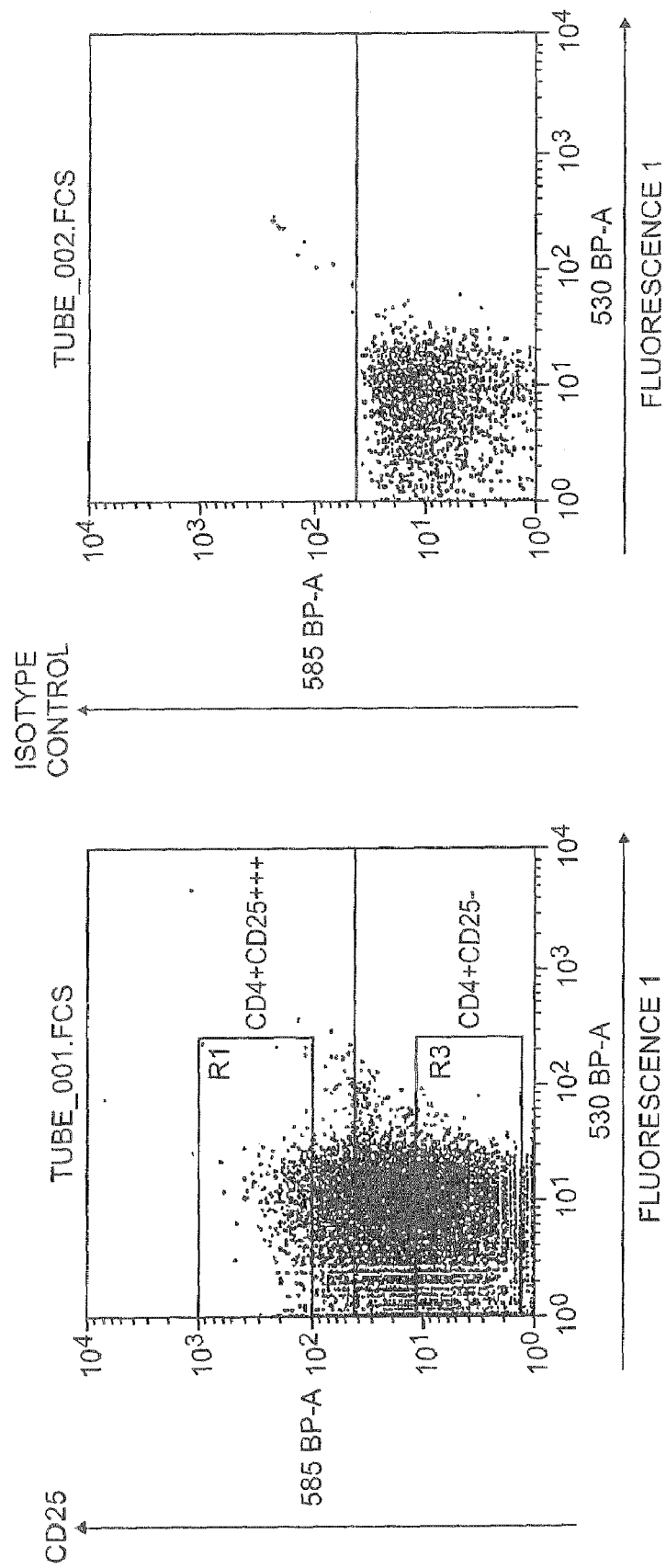

In FIG. 18 are shown the results of a therapy of the passive or active adoptive transfer EAN (AT-EAN). This is not induced by immunization with the nerve antigen, as described above, but takes place by intravenous injection of an autoreactive CD4+ T cell clone with specificity for the P2 myelin antigen (8·10$^6$, cell line G7) according to the document Stienekemeier et al., Brain, 122:523-535 (1999). FIG. 18*a* shows the course of the disease of a control group, under treatment with JJ316 at day 1 (d1) and treatment at day 3 (d3). It is notable that even after the beginning of the disease symptoms, i.e. treatment at day 3, the disease can be stopped. In FIG. 18*b* the infiltration of the nerves with T cells has been quantified for the three groups, and it can be seen that in the control group this leads to a damage to the nerves. In contrast, the T cell counts are considerably lower in case of a treatment with mAbs used according to the invention because of the induction of regulatory T cells.

In the experiments of FIGS. 19 to 22, it is finally proven that CD4+CD25+++ T cells expanded by means of monoclonal antibodies according to the invention can even after expansion maintain their functional properties, e.g. the suppression of the proliferation of "conventional" T cells. For this purpose, the CD4+ T cells from human peripheral mononuclear cells (PBMC) were purified by means of magnetic separation (negative depletion of CD8+, CD11b+, CD16+, CD19+, CD36+ and CD56+ cells; purity 95%). These cells were then loaded with a CD28-specific antibody and then with a PE-conjugated secondary antibody, sorted into CD4+CD25+++ and CD4+CD25− T cells (see FIG. 19) and cultivated after addition of monoclonal antibodies according to the invention coupled to Dynabeads (huIgG4) and Interleukin 2 (IL-2) (day 0). On day 5, a coloration of the expanded cells with anti-CD4 and anti-CD25 at the cell surface took place, and intracellularly with anti-CTLA-4 and Ki-67. On day 6, the separation of the beads from the cultivated cells and removal of the IL-2 by repeated washing was performed, followed by a 2-day culture in medium alone. The two subpopulations multiplied tenfold within 8 days (see FIG. 20).

The increased expression of the protein CTLA-4 in the expanded CD4+CD25+++ cells (see FIG. 21) is an indication that these cells have kept their regulatory phenotype. This was then verified as follows by a functional characterization.

Figure 22B:
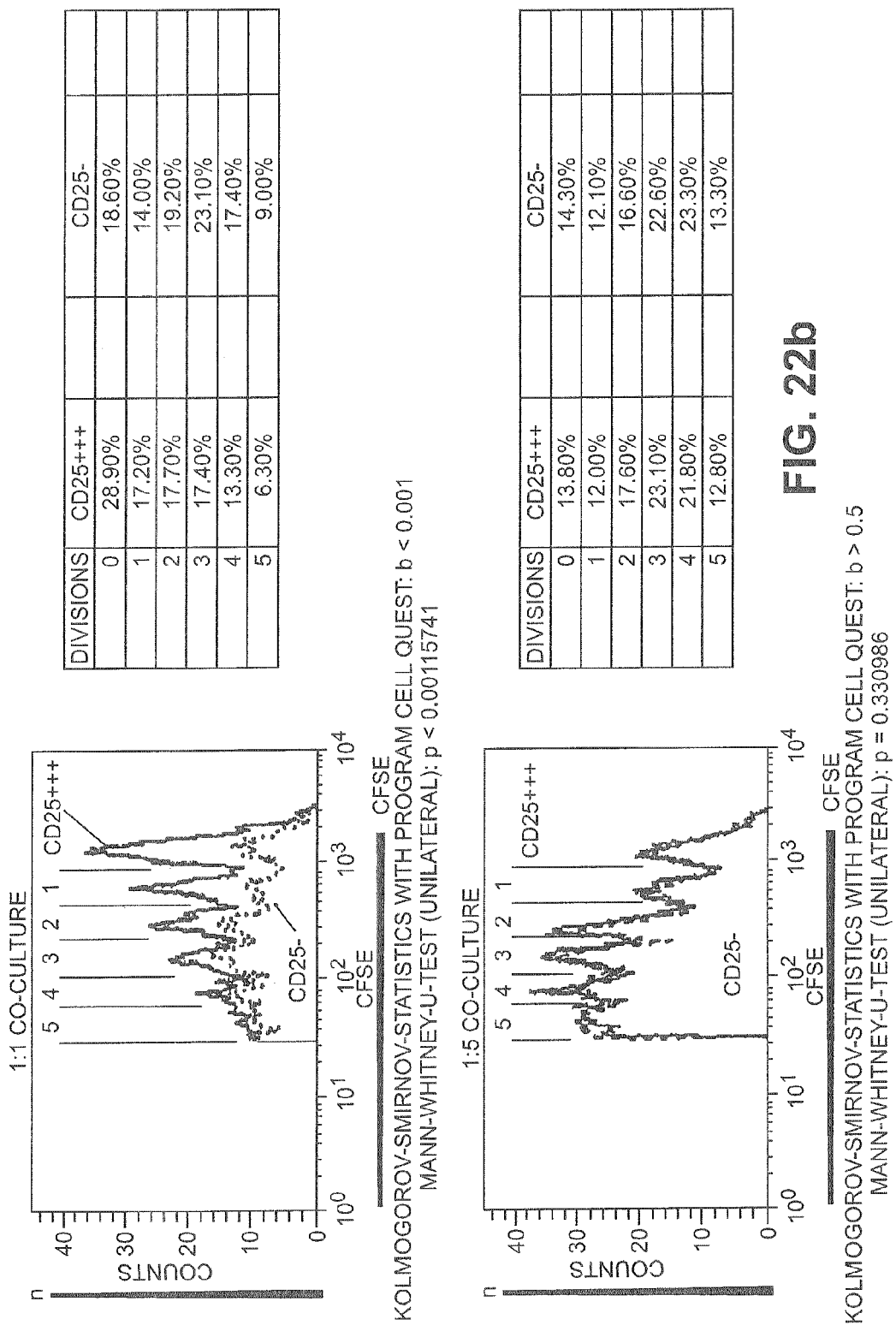

Syngeneic peripheral mononuclear cells from heparinized whole blood were gained and marked with the fluorescence dye CFSE (carboxy fluorescencein diacetate succinimidyl ester). These cells served as indicators cells. Firstly, they were stimulated with anti-CD3 and anti-CD28 antibodies for three days. With every cell division, the intensity of the marking measurement values of these indicator cells were halved (see FIG. 22*a*). In independent approaches, on day 8 expanded CD4+CD25+++ or CD4+CD25− T cells, resp., were mixed with the CFSE-marked indicator cells in a ratio 1:1 or 1:5, resp., and were cultivated (stimulation with anti-CD3 mAb, clone HIT3a, final concentration 0.1 µg/ml and anti-CD28 mAb, clone CD28.2, final concentration 0.05 µg/ml). FIG. 22*b* shows that the number of cell divisions in the indicator cells was strongly reduced by the presence of the expanded CD4+CD25+++ T cells, whereas the CD4+CD25− T cells showed a weak effect only. Thus it is proven that the regulatory CD4+CD25+++ T cells expanded with monoclonal antibodies according to the invention were still able to suppress the proliferation of other "normal" T cells.

TABLE I

Binding of anti-rat CD28 mAbs to mouse and rat CD28 and different CD28 mutants

| mAb | mouse CD28 | rat CD28 | mcD28, S62P A64V, E65G | m/rCD28 Mva1269I |
|---|---|---|---|---|
| Contr. | − | − | − | − |
| JJ316 | − | +++ | +++ | − |
| JJ319 | − | +++ | − | +++ |
| 5S28 | − | ++ | − | ++ |
| 5S38.17 | − | +++ | +++ | − |
| 5S247 | − | +++ | − | +++ |
| 5G40/3 | − | +++ | − | +++ |
| 5G87 | − | ++ | − | ++ |
| 5G111 | − | ++ | − | ++ |
| 5S35 | − | +++ | + | +++ |

The invention claimed is:

1. A method for the treatment of Guillain-Barré syndrome or chronic demyelinating polyneuropathy, wherein a body liquid is taken from a patient, comprising blood comprising T lymphocytes or precursor cells hereto, and the body liquid is reacted with a CD28-specific superagonistic monoclonal antibody or a mimicry compound hereto, and the thus treated body liquid is again administered to the patient.

2. The method of claim 1, wherein the body liquid is administered to the patient by intraveneous injection.

* * * * *

SEQUENCE LISTING

```
<160> NUMBER OF SEQ ID NOS: 19

<210> SEQ ID NO 1
<211> LENGTH: 6
<212> TYPE: PRT
<213> ORGANISM: homo sapiens

<400> SEQUENCE: 1

Val Tyr Ser Lys Thr Gly
1               5

<210> SEQ ID NO 2
<211> LENGTH: 4
<212> TYPE: PRT
<213> ORGANISM: homo sapiens

<400> SEQUENCE: 2

Tyr Ser Lys Thr
1

<210> SEQ ID NO 3
```

```
<211> LENGTH: 5
<212> TYPE: PRT
<213> ORGANISM: homo sapiens

<400> SEQUENCE: 3

Tyr Ser Lys Thr Gly
1               5

<210> SEQ ID NO 4
<211> LENGTH: 5
<212> TYPE: PRT
<213> ORGANISM: homo sapiens

<400> SEQUENCE: 4

Val Tyr Ser Lys Thr
1               5

<210> SEQ ID NO 5
<211> LENGTH: 6
<212> TYPE: PRT
<213> ORGANISM: homo sapiens

<400> SEQUENCE: 5

Tyr Ser Lys Thr Gly Phe
1               5

<210> SEQ ID NO 6
<211> LENGTH: 7
<212> TYPE: PRT
<213> ORGANISM: homo sapiens

<400> SEQUENCE: 6

Val Tyr Ser Lys Thr Gly Phe
1               5

<210> SEQ ID NO 7
<211> LENGTH: 5
<212> TYPE: PRT
<213> ORGANISM: homo sapiens

<400> SEQUENCE: 7

Ser Lys Thr Gly Phe
1               5

<210> SEQ ID NO 8
<211> LENGTH: 8
<212> TYPE: PRT
<213> ORGANISM: homo sapiens

<400> SEQUENCE: 8

Gly Asn Tyr Ser Gln Gln Leu Gln
1               5

<210> SEQ ID NO 9
<211> LENGTH: 321
<212> TYPE: DNA
<213> ORGANISM: artificial
<220> FEATURE:
<221> NAME/KEY: msic_feature
<222> LOCATION: (1)..(321)
<223> OTHER INFORMATION: mab

<400> SEQUENCE: 9
gatatccaga cgacacagac tacatcctcc cgttctgcct ctctgggaga cagagtcacc      60
atcagttgca gggcaggtca ggacattagt aattatttaa actggtatca gcagaaacca     120
```

```
gatggaactg ttaagctcct gatctactac acatcaagat tacactcagg agtcccatca    180
aggttcagtg gcagtgggtc tggaacagat tattctctca ccattagcaa cctggagcaa    240
gaagatattg ccacttactt ttgccaacag ggtcatacgc ttccgtggac gttcggtgga    300
ggcaccaagc tggaaatcaa a                                              321
```

<210> SEQ ID NO 10
<211> LENGTH: 107
<212> TYPE: PRT
<213> ORGANISM: artificial
<220> FEATURE:
<221> NAME/KEY: misc_feature
<222> LOCATION: (1)..(107)
<223> OTHER INFORMATION: mab

<400> SEQUENCE: 10

```
Asp Ile Gln Thr Thr Gln Thr Thr Ser Ser Leu Ser Ala Ser Leu Gly
1               5                   10                  15

Asp Arg Val Thr Ile Ser Cys Arg Ala Gly Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly His Thr Leu Pro Trp
                85                  90                  95

Thr Phe Gly Gly Gly Thr Lys Leu Glu Ile Lys
            100                 105
```

<210> SEQ ID NO 11
<211> LENGTH: 363
<212> TYPE: DNA
<213> ORGANISM: artificial
<220> FEATURE:
<221> NAME/KEY: misc_feature
<222> LOCATION: (1)..(363)
<223> OTHER INFORMATION: mab

<400> SEQUENCE: 11

```
gatgtgcagc ttcaggagtc gggacctggc ctggtgaaac cttctcagtc tctgtccctc     60
acctgcactg tcactggcta ctcaatcacc agtgattatg cctggaactg gatccggcag    120
tttccaggaa acaaactgga gtggatgggc tacataagat acagtggtag tactagctac    180
aatccatctc tcaaaagtcg aatctctatc actcgagaca catccaagaa ccagttcttc    240
ctgcagttga attctgtgac tactgaggac acagccacat attactgtgc aagagattgg    300
ccgcgaccga gctactggta cttcgatgtc tggggcgcag ggaccacggt caccgtctcc    360
tca                                                                  363
```

<210> SEQ ID NO 12
<211> LENGTH: 121
<212> TYPE: PRT
<213> ORGANISM: artificial
<220> FEATURE:
<221> NAME/KEY: misc_feature
<222> LOCATION: (1)..(121)
<223> OTHER INFORMATION: mab

<400> SEQUENCE: 12

```
Asp Val Gln Leu Gln Glu Ser Gly Pro Gly Leu Val Lys Pro Ser Gln
```

```
                1               5                   10                  15
Ser Leu Ser Leu Thr Cys Thr Val Thr Gly Tyr Ser Ile Thr Ser Asp
                    20                  25                  30

Tyr Ala Trp Asn Trp Ile Arg Gln Phe Pro Gly Asn Lys Leu Glu Trp
            35                  40                  45

Met Gly Tyr Ile Arg Tyr Ser Gly Ser Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Asp Trp Pro Arg Pro Ser Tyr Trp Tyr Phe Asp Val Trp Gly
            100                 105                 110

Ala Gly Thr Thr Val Thr Val Ser Ser
            115                 120

<210> SEQ ID NO 13
<211> LENGTH: 360
<212> TYPE: DNA
<213> ORGANISM: artificial
<220> FEATURE:
<221> NAME/KEY: misc_feature
<222> LOCATION: (1)..(360)
<223> OTHER INFORMATION: mab

<400> SEQUENCE: 13
caggtccaac tgcagcagtc cggacctgag ctggtgaagc cggggacttc agtgaggatt      60
tcctgcgagg cttctggcta caccttcaca agctactata tacactgggt gaaacagagg     120
cctggacagg gacttgagtg gattggatgt atttatcctg gaaatgtcaa tactaactat     180
aatgagaagt tcaaggacaa ggccacactg attgtagaca catcctccaa cactgcctac     240
atgcagctca gcagaatgac ctctgaggac tctgcggtct atttctgtac aagatcacac     300
tacggcctcg actggaactt cgatgtctgg ggcgcaggga ccacggtcac cgtctcctca     360

<210> SEQ ID NO 14
<211> LENGTH: 120
<212> TYPE: PRT
<213> ORGANISM: artificial
<220> FEATURE:
<221> NAME/KEY: misc_feature
<222> LOCATION: (1)..(120)
<223> OTHER INFORMATION: mab

<400> SEQUENCE: 14

Gln Val Gln Leu Gln Gln Ser Gly Pro Glu Leu Val Lys Pro Gly Thr
1               5                   10                  15

Ser Val Arg Ile Ser Cys Glu Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Cys Ile Tyr Pro Gly Asn Val Asn Thr Asn Tyr Asn Glu Lys Phe
    50                  55                  60

Lys Asp Lys Ala Thr Leu Ile Val Asp Thr Ser Ser Asn Thr Ala Tyr
65                  70                  75                  80

Met Gln Leu Ser Arg Met Thr Ser Glu Asp Ser Ala Val Tyr Phe Cys
                85                  90                  95

Thr Arg Ser His Tyr Gly Leu Asp Trp Asn Phe Asp Val Trp Gly Ala
            100                 105                 110
```

Gly Thr Thr Val Thr Val Ser Ser
        115                 120

<210> SEQ ID NO 15
<211> LENGTH: 321
<212> TYPE: DNA
<213> ORGANISM: artificial
<220> FEATURE:
<221> NAME/KEY: misc_feature
<222> LOCATION: (1)..(321)
<223> OTHER INFORMATION: mab

<400> SEQUENCE: 15
gacatccaga tgaaccagtc tccatccagt ctgtctgcat cccttggaga cacaattacc      60
atcacttgcc atgccagtca aaacatttat gtttggttaa actggtacca gcagaaacca     120
ggaaatattc ctaaactctt gatctataag gcttccaacc tgcacacagg cgtcccatca     180
aggtttagtg gcagtggatc tggaacaggc ttcacattaa ccatcagcag cctgcagcct     240
gaagacattg ccacttacta ctgtcaacag ggtcaaactt atccgtacac gttcggaggg     300
gggaccaagc tggaaataaa a                                               321

<210> SEQ ID NO 16
<211> LENGTH: 107
<212> TYPE: PRT
<213> ORGANISM: artificial
<220> FEATURE:
<221> NAME/KEY: misc_feature
<222> LOCATION: (1)..(107)
<223> OTHER INFORMATION: mab

<400> SEQUENCE: 16

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Tyr Val Trp
            20                  25                  30

Leu Asn Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Thr Tyr Pro Tyr
                85                  90                  95

Thr Phe Gly Gly Gly Thr Lys Leu Glu Ile Lys
            100                 105

<210> SEQ ID NO 17
<211> LENGTH: 15
<212> TYPE: PRT
<213> ORGANISM: homo sapiens

<400> SEQUENCE: 17

Gly Asn Tyr Ser Gln Gln Leu Gln Val Tyr Ser Lys Thr Gly Phe
1               5                   10                  15

<210> SEQ ID NO 18
<211> LENGTH: 107
<212> TYPE: PRT
<213> ORGANISM: artificial
<220> FEATURE:
<221> NAME/KEY: misc_feature
<222> LOCATION: (1)..(107)
<223> OTHER INFORMATION: mab

```
<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
                100                 105

<210> SEQ ID NO 19
<211> LENGTH: 120
<212> TYPE: PRT
<213> ORGANISM: artificial
<220> FEATURE:
<221> NAME/KEY: misc_feature
<222> LOCATION: (1)..(120)
<223> OTHER INFORMATION: mab

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
                100                 105                 110

Gly Thr Thr Val Thr Val Ser Ser
                115                 120
```